US010149840B2

(12) United States Patent
Yamashita et al.

(10) Patent No.: US 10,149,840 B2
(45) Date of Patent: Dec. 11, 2018

(54) OCT3 ACTIVITY INHIBITOR CONTAINING IMIDAZOPYRIDINE DERIVATIVE AS ACTIVE COMPONENT, AND OCT3 DETECTION AGENT

(71) Applicant: SHIN NIPPON BIOMEDICAL LABORATORIES, LTD., Kagoshima-shi, Kagoshima (JP)

(72) Inventors: Hidetoshi Yamashita, Kagoshima (JP); Nobuyuki Suzuki, Kagoshima (JP)

(73) Assignee: SHIN NIPPON BIOMEDICAL LABORATORIES, LTD., Kagoshima (JP)

( * ) Notice: Subject to any disclaimer, the term of this patent is extended or adjusted under 35 U.S.C. 154(b) by 0 days.

(21) Appl. No.: 15/705,296

(22) Filed: Sep. 15, 2017

(65) Prior Publication Data

US 2018/0000797 A1  Jan. 4, 2018

Related U.S. Application Data

(62) Division of application No. 14/655,729, filed as application No. PCT/JP2013/083759 on Dec. 17, 2013.

(30) Foreign Application Priority Data

Dec. 28, 2012 (JP) ................. 2012-287682

(51) Int. Cl.
*A61K 31/437* (2006.01)
*A61K 31/496* (2006.01)
*A61K 31/4453* (2006.01)
*C07D 471/04* (2006.01)
*A61K 31/444* (2006.01)

(52) U.S. Cl.
CPC .......... *A61K 31/437* (2013.01); *A61K 31/444* (2013.01); *A61K 31/4453* (2013.01); *A61K 31/496* (2013.01); *C07D 471/04* (2013.01)

(58) Field of Classification Search
CPC ................ A61K 31/437; A61K 31/444; A61K 31/4453; A61K 31/496; C07D 471/04
USPC ........................................ 546/121
See application file for complete search history.

(56) References Cited

U.S. PATENT DOCUMENTS

| 6,403,645 | B2 | 6/2002 | Schildkraut et al. | |
|---|---|---|---|---|
| 2007/0136828 | A1 | 6/2007 | Kitaichi | |
| 2008/0051409 | A1* | 2/2008 | Gmeiner | C07D 471/04 514/252.02 |
| 2009/0149494 | A1 | 6/2009 | Peyronel | |
| 2009/0176778 | A1 | 7/2009 | Schmitz et al. | |
| 2010/0016303 | A1 | 1/2010 | Ritzen et al. | |
| 2010/0168155 | A1 | 7/2010 | El-Ahmad et al. | |
| 2010/0317620 | A1 | 12/2010 | Peyronel | |
| 2010/0317673 | A1 | 12/2010 | Peyronel | |

FOREIGN PATENT DOCUMENTS

| JP | WO2005084707 A1 | 9/2005 |
|---|---|---|
| JP | WO2008047883 A1 | 4/2008 |
| JP | 2009-541473 A | 11/2009 |
| JP | 2011-509251 A | 3/2011 |
| WO | WO2001093863 A2 | 12/2001 |
| WO | WO2008029152 A2 | 3/2008 |
| WO | WO2009134877 A2 | 11/2009 |
| WO | WO2010139966 A1 | 12/2010 |
| WO | WO2012006203 A1 | 1/2012 |
| WO | WO2012080729 A2 | 6/2012 |

OTHER PUBLICATIONS

Koepsell; Pharmaceutical Research 2007, 24, 1227-1251. DOI: 10.1007/s11095-007-9254-z (Year: 2007).*
Koepsell; Molecular Aspects of Medicine 2013, 34, 413-435. Available online Mar. 16, 2013. DOI:10.1016/j.mam.2012.10.010 (Year: 2013).*
Koubachi; Tetrahedron 66 (2010) 1937-1946. (Year: 2010).*
Tiago Rodrigues et al : "Identification of new antimalarial leads by use of virtual screening against cytochrome", Bioorganic & Medical Chemistry, Pergamon, GB, vol. 19, No. 21, Sep. 5, 2011; pp. 6302-6308, XP028316321.
Bruce A E Cynthia et al: Issue in Honor of Drs *Pseudomonas aeruginosa* porphobilinogen synthase assembly state regulators: hit discovery and initial SAR studies, ARKIVOC, Jan. 1, 2010, pp. 175-188, XP055286645.
Laufer S et al: "Investigations of SCIO-469-like compounds for the inhibition of p38 MAP kinase", Bioorganic & Medicinal Chemistry Letters, Pergamon, NL, vol. 19, No. 5, Mar. 1, 2009, pp. 1461-1464, XP025951162.
Yifeng Xiong et al: "Identification of fused bicyclic heterocycles as potent and selective 5-HTreceptor antagonists for the treatment of insomnia", Bioorganic & Medicinal Chemistry Letters, Pergamon, NL, vol. 22, No. 5, Jan. 20, 2012, pp. 1870-1873; XP028459418.
Jean Michel Chezal et al: "Evaluation of Radiolabeled (Hetero) Aromatic Analogues of N-(2-diethylaminoethyl)-4-iodobenzamide for Imaging and Targeted Radionuclide Therapy of Melanoma", Journal of Medicinal Chemistry, American Chemical Society, US, vol. 51, No. 11, Jan. 1, 2008, pp. 3133-3144, XP008145470.
Aurélie Maisonial et al: "Single Photon Emission Computed Tomography/Positron Emission Tomography Imaging and Targeted Radionuclide Therapy of Melanoma: New Multimodal Fluorinated and Iodinated Radiotracers", Jounal of Medicinal Chemistry, vol. 54, No. 8, Apr. 28, 2011, pp. 2745-2766, XP055250303.
Grassy G et al: "Inhibitory effects on platelet aggregation and cyclic AMP phosphodiesterase of azaindolizine-type compounds", Chemometrics and Intelligent Laboratory Systems, Elsevier Science Publishers B.V. Amsterdam, NL, vol. 20, No. 1, Aug. 1, 1993, pp. 71-84, XP026502520.

(Continued)

*Primary Examiner* — Daniel R Carcanague
(74) *Attorney, Agent, or Firm* — Pyprus Pte Ltd

(57) ABSTRACT

To provide an OCT3 activity inhibitor having a different basic skeleton than that of conventional OCT3 activity inhibitors. This inhibitor of organic cation transporter 3 (OCT3) contains, as an active component, an imidazo[1,2-a]pyridine derivative, a pharmaceutically acceptable salt thereof, or a pharmaceutically acceptable solvate thereof.

4 Claims, No Drawings

(56) References Cited

OTHER PUBLICATIONS

Extended European Search Report for EP application No. 13868302.4 dated Aug. 17, 2016 (17 pages).
International Search Report of International application No. PCT/JP2013/083759 completed Mar. 19, 2014 and dated Apr. 1, 2014 (4 pages).
Hao-Jie Zhu et al, Evaluation of organic cation transporter 2 (SLC22A3) inhibition as a potential mechanism of antidepressant action, Pharmcol Res., Apr. 2012, 65 (4), 491-6.
Nies, Handb Exp Pharmacol v201, 2011, p. 105-167.
Sata, J Pharmacol Exp Ther., v315, 2005, p. 888-895.
Chemical Abstracts STN Registry Database record for RN 1259134-82-1 entered Jan. 12, 2011.
Chemical Abstracts STN Registry Database record for RN 1258762-08-1 entered Jan. 7, 2011.
Chemical Abstracts STN Registry Database record for RN 1241580-59-5 entered Sep. 16, 2010.
Chemical Abstracts STN Registry Database record for RN 1241193-31-6 entered Sep. 15, 2010.
Chemical Abstracts STN Registry Database record for RN 1111504-98-3 entered Feb. 25, 2009.
Chemical Abstracts STN Registry Database record for RN 1009428-15-2 entered Mar. 21, 2008.
Chemical Abstracts STN Registry Database record for RN 1009428-43-6 entered Mar. 21, 2008.
Chemical Abstracts STN Registry Database record for RN 914227-58-0 entered Nov. 29, 2006.
Chemical Abstracts STN Registry Database record for RN 1111448-61-3 entered Feb. 25, 2009.
Chemical Abstracts STN Registry Database record for RN 1015525-53-7 entered Apr. 18, 2008.
Chemical Abstracts STN Registry Database record for RN 931610-17-2 entered Apr. 22, 2007.
Chemical Abstracts STN Registry Database record for RN 1009890-64-5 entered Mar. 25, 2008.
Chemical Abstracts STN Registry Database record for RN 949777-41-7 entered Oct. 9, 2007.
Chemical Abstracts STN Registry Database record for RN 941170-40-7 entered Jul. 4, 2007.
Chemical Abstracts STN Registry Database record for RN 931650-19-0 entered Apr. 22, 2007.
Chemical Abstracts STN Registry Database record for RN 1081134-73-7 entered Dec. 7, 2008.
Chemical Abstracts STN Registry Database record for RN 1223423-21-9 entered May 14, 2010.
Chemical Abstracts STN Registry Database record for RN 924167-47-5 entered Mar. 1, 2007.
Chemical Abstracts STN Registry Database record for RN 930918-49-3 entered Apr. 19, 2007.
Chemical Abstracts STN Registry Database record for RN 570361-50-1 entered Aug. 21, 2003.
Chemical Abstracts STN Registry Database record for RN 1111532-00-3 entered Feb. 25, 2009.
Chemical Abstracts STN Registry Database record for RN 570361-54-5 entered Aug. 21, 2003.
Chemical Abstracts STN Registry Database record for RN 1010032-80-0 entered Mar. 26, 2008.
Chemical Abstracts STN Registry Database record for RN 1240859-69-1 entered Sep. 14, 2010.
Chemical Abstracts STN Registry Database record for RN 924429-58-3 entered Mar. 2, 2007.
Chemical Abstracts STN Registry Database record for RN 1010501-41-3 entered Mar. 27, 2008.
Chemical Abstracts STN Registry Database record for RN 1111465-73-6 entered Feb. 25, 2009.

* cited by examiner

OCT3 ACTIVITY INHIBITOR CONTAINING IMIDAZOPYRIDINE DERIVATIVE AS ACTIVE COMPONENT, AND OCT3 DETECTION AGENT

TECHNICAL FIELD

The present invention relates to an organic cation transporter 3 (OCT3) activity inhibitor containing an imidazopyridine derivative as an active component, and an OCT3 detection agent.

BACKGROUND ART

Various pharmaceutical agents are used in a drug therapy. Some of these agents become positive ions (cations) under biological conditions. Recently, a study of a transporter (transport protein), which exists in a cell membrane and contributes to migration of a pharmaceutical agent to a tissue, absorption thereof, renal excretion thereof and biliary excretion thereof by transporting the pharmaceutical agent actively, has been significantly advanced. Among the transporters, an organic cation transporter (OCT) is important to transport a cationic pharmaceutical agent.

Recent studies have revealed that an OCT3 exists not only in the placenta, but also in the kidneys, the small intestine, the lungs, the heart, and the brain.

A nucleoside derivative, a quinoline derivative, and a compound having a tricyclic structure have been reported as OCT3 activity inhibitors. However, it is difficult to use these compounds as drugs because of side effects etc. thereof. In addition, a guanidine derivative has been reported as the OCT3 activity inhibitor (Non Patent Literature 1 described below). However, it has been reported that $IC_{50}$s of famotidine and cimetidine (histamine H2 receptor antagonists) are 20 μM and 240 μM, respectively, and that $IC_{50}$s of ramosetron and granisetron (setron-based compounds) are both 100 μM or less.

Meanwhile, WO 2005/084707 A (Patent Literature 1) discloses a therapeutic agent for mental disorder, containing a substance suppressing expression of an organic cation transporter OCT3 gene as an active component. US 2007/0136828 (Patent Literature 2) discloses a therapeutic agent for depression by inhibiting a function of the OCT3, containing an antisense nucleic acid of the OCT3 gene. WO 2009/134877 A (Patent Literature 3) discloses a therapeutic agent for depression by inhibiting a function of the OCT3, containing an alkylamine-catechol derivative, a quinoline derivative, and a bis-quinoline derivative as active components. WO 2001/93863 A (Patent Literature 4) discloses a therapeutic agent for depression and symptoms suggesting depression, containing famotidine as an active component. U.S. Pat. No. 6,403,645 (Patent Literature 5) discloses a therapeutic agent for depression, containing a transporter Uptake2 (OCT and PMAT) inhibitor as an active component.

According to these literatures, it has been established that depression and symptoms suggesting depression can be treated by inhibiting the organic cation transporter OCT3.

These pharmaceutical agents are disadvantageous in view of intracerebral transferability and nephrotoxicity. Therefore, development of a novel OCT3 activity inhibitor having a completely different basic structure has been desired. In addition, development of an OCT3 detection agent has been desired.

A medicine containing an imidazo[1,2-a]pyridine derivative as an active component is known. For example, Zolpidem (registered trademark) is a therapeutic agent for insomnia, which acts on a ω1-type $GABA_A$ receptor. Alpidem (registered trademark) is an anxiolytic drug which acts on a peripheral benzodiazepine receptor. Zolimidin (registered trademark) is an antiulcer drug. Olprinone (registered trademark) is a therapeutic agent for acute heart failure, which inhibits PDE3.

CITATION LIST

Patent Literatures

Patent Literature 1: WO 2005/084707 A
Patent Literature 2: US 2007/0136828
Patent Literature 3: WO 2009/134877 A
Patent Literature 4: WO 2001/93863 A
Patent Literature 5: U.S. Pat. No. 6,403,645

Non Patent Literatures

Non Patent Literature 1: Nies, 2011, Handb Exp Pharmacol., v201, p 105-167 Nies, 2011, Handb Exp Pharmacol., v201, p 105-167
Non Patent Literature 2: Sata, 2005, J Pharmacol Exp Ther., v315, p 888-895 Sata, 2005, J Pharmacol Exp Ther., v315, p 888-895

SUMMARY OF INVENTION

Technical Problem

An object of the present invention is to provide an OCT3 activity inhibitor having a different basic structure from the OCT3 activity inhibitor in the related art.

Another object of the present invention is to provide a therapeutic agent for a disease relating to the OCT3.

Still another object of the present invention is to provide an OCT3 detection agent.

Solution to Problem

The present invention is basically based on the finding that an imidazopyridine derivative (particularly imidazo[1,2-a]pyridine derivative) has a bonding function to the OCT3 and an OCT3 activity-inhibiting function.

A first aspect of the present invention relates to an organic cation transporter 3 (OCT3) inhibitor containing, as an active component, a compound represented by formula (I), a pharmaceutically acceptable salt thereof, or a pharmaceutically acceptable solvate thereof.

[Chemical Formula 1]

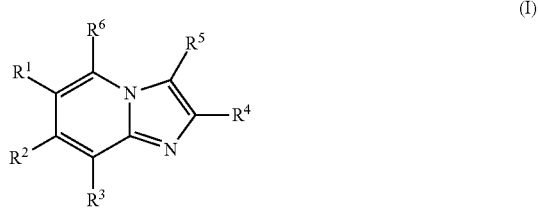

In formula (I), $R^1$ to $R^3$, $R^5$ and $R^6$ may be the same or different, and each represent a hydrogen atom, a halogen atom, a $C_{1-3}$ alkyl group, a $C_{1-3}$ alkoxy group, a $C_{1-3}$ alkylthio group, or a $C_{1-3}$ halogenoalkyl group. $R^4$ represents any of the groups represented by formulae (II) to (VII).

[Chemical Formula 2]

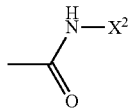

(II)

In formula (II), $X^2$ represents a $C_{1-10}$ alkyl group which may have a substituent, a $C_{1-10}$ alkoxy group which may have a substituent, a $C_{1-10}$ alkylthio group which may have a substituent, a $C_{2-10}$ alkenyl group which may have a substituent, or a $C_{2-10}$ alkynyl group which may have a substituent.

[Chemical Formula 3]

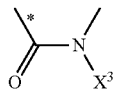

(III)

In formula (III), $X^3$ represents a $C_{1-10}$ alkyl group which may have a substituent, a $C_{1-10}$ alkoxy group which may have a substituent, a $C_{1-10}$ alkylthio group which may have a substituent, a $C_{2-10}$ alkenyl group which may have a substituent, or a $C_{2-10}$ alkynyl group which may have a substituent. Note that a symbol (*) is given to a bonding portion to the carbon atom (C) adjacent to $R^4$ in formula (III).

[Chemical Formula 4]

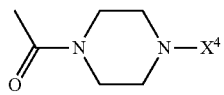

(IV)

In formula (VI), $X^4$ represents a $C_{1-10}$ alkyl group which may have a substituent, a $C_{1-10}$ alkoxy group which may have a substituent, a $C_{1-10}$ alkylthio group which may have a substituent, a $C_{2-10}$ alkenyl group which may have a substituent, a $C_{2-10}$ alkynyl group which may have a substituent, or a $C_{6-12}$ aryl group which may have a substituent.

[Chemical Formula 5]

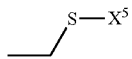

(V)

In formula (V), $X^5$ represents a $C_{1-10}$ alkyl group which may have a substituent, a $C_{1-10}$ alkoxy group which may have a substituent, a $C_{1-10}$ alkylthio group which may have a substituent, a $C_{2-10}$ alkenyl group which may have a substituent, a $C_{2-10}$ alkynyl group which may have a substituent, a 5-membered ring group which may have a substituent, or a $C_{6-12}$ aryl group which may have a substituent.

[Chemical Formula 6]

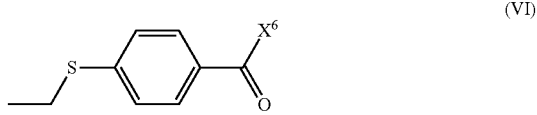

(VI)

In formula (VI), $X^6$ represents a $C_{1-10}$ alkyl group which may have a substituent, a $C_{1-10}$ alkoxy group which may have a substituent, a $C_{1-10}$ alkylthio group which may have a substituent, a $C_{2-10}$ alkenyl group which may have a substituent, a $C_{2-10}$ alkynyl group which may have a substituent, a 5-membered ring group which may have a substituent, or a $C_{6-12}$ aryl group which may have a substituent.

[Chemical Formula 7]

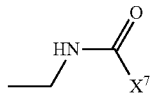

(VII)

In formula (VII), $X^7$ represents a $C_{1-10}$ alkyl group which may have a substituent, a $C_{1-10}$ alkoxy group which may have a substituent, a $C_{1-10}$ alkylthio group which may have a substituent, a $C_{2-10}$ alkenyl group which may have a substituent, a $C_{2-10}$ alkynyl group which may have a substituent, a 5-membered ring group which may have a substituent, or a $C_{6-12}$ aryl group which may have a substituent.

A second aspect of the present invention relates to a therapeutic agent for mental disorder, containing any of the above-described "organic cation transporter 3 (OCT3) inhibitors" as an active component. More specifically, this aspect relates to a therapeutic agent for depression, containing any of the above-described organic cation transporter 3 (OCT3) inhibitors as an active component.

A third aspect of the present invention relates to an organic cation transporter 3 (OCT3) detection agent.

Advantageous Effects of Invention

According to the present invention, it is possible to provide an OCT3 activity inhibitor having a different basic structure from the OCT3 activity inhibitor in the related art.

In addition, the present invention can provide a therapeutic agent for a disease relating to the OCT3.

Furthermore, the present invention can provide an OCT3 detection agent.

DESCRIPTION OF EMBODIMENTS

A first aspect of the present invention relates to an organic cation transporter 3 (OCT3) inhibitor containing, as an active component, a compound represented by formula (I) (the compound of the present invention), a pharmaceutically acceptable salt thereof, or a pharmaceutically acceptable solvate thereof. As illustrated in the following formula (I), the compound of the present invention is an imidazopyridine derivative. More specifically, the compound of the present invention is an imidazo[1,2-a]pyridine derivative.

[Chemical Formula 8]

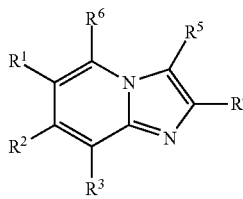

(I)

In formula (I), $R^1$ to $R^3$, $R^5$ and $R^6$ may be the same or different, and each represent a hydrogen atom, a halogen atom, a $C_{1-3}$ alkyl group, a $C_{1-3}$ alkoxy group, a $C_{1-3}$ alkylthio group, or a $C_{1-3}$ halogenoalkyl group. Preferable examples of $R^1$ to $R^3$, $R^5$, and $R^6$ include a hydrogen atom and a $C_{1-3}$ alkyl group. Here, the $C_{1-3}$ alkyl group is preferably a methyl group or an ethyl group.

$R^4$ represents any of the groups represented by formulae (II) to (VII).

[Chemical Formula 9]

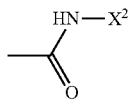

(II)

In formula (II), $X^2$ represents a $C_{1-10}$ alkyl group which may have a substituent, a $C_{1-10}$ alkoxy group which may have a substituent, a $C_{1-10}$ alkylthio group which may have a substituent, a $C_{2-10}$ alkenyl group which may have a substituent, a $C_{2-10}$ alkynyl group which may have a substituent, a $C_{6-10}$ aryl group which may have a substituent, or a $C_{7-10}$ aralkyl group which may have a substituent.

[Chemical Formula 10]

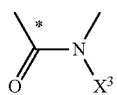

(III)

In formula (III), $X^3$ represents a $C_{1-10}$ alkyl group which may have a substituent, a $C_{1-10}$ alkoxy group which may have a substituent, a $C_{1-10}$ alkylthio group which may have a substituent, a $C_{2-10}$ alkenyl group which may have a substituent, or a $C_{2-10}$ alkynyl group which may have a substituent. Note that a symbol (*) is given to a bonding portion to the carbon atom (C) adjacent to $R^4$ in formula (III).

[Chemical Formula 11]

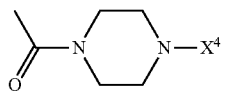

(IV)

In formula (VI), $X^4$ represents a $C_{1-10}$ alkyl group which may have a substituent, a $C_{1-10}$ alkoxy group which may have a substituent, a $C_{1-10}$ alkylthio group which may have a substituent, a $C_{2-10}$ alkenyl group which may have a substituent, a $C_{2-10}$ alkynyl group which may have a substituent, or a $C_{6-12}$ aryl group which may have a substituent.

[Chemical Formula 12]

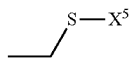

(V)

In formula (V), $X^5$ represents a $C_{1-10}$ alkyl group which may have a substituent, a $C_{1-10}$ alkoxy group which may have a substituent, a $C_{1-10}$ alkylthio group which may have a substituent, a $C_{2-10}$ alkenyl group which may have a substituent, a $C_{2-10}$ alkynyl group which may have a substituent, a 5-membered ring group which may have a substituent, or a $C_{6-12}$ aryl group which may have a substituent.

[Chemical Formula 13]

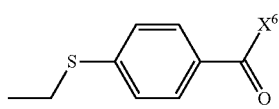

(VI)

In formula (VI), $X^6$ represents a $C_{1-10}$ alkyl group which may have a substituent, a $C_{1-10}$ alkoxy group which may have a substituent, a $C_{1-10}$ alkylthio group which may have a substituent, a $C_{2-10}$ alkenyl group which may have a substituent, a $C_{2-10}$ alkynyl group which may have a substituent, a 5-membered ring group which may have a substituent, or a $C_{6-12}$ aryl group which may have a substituent.

[Chemical Formula 14]

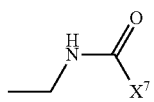

(VII)

In formula (VII), $X^7$ represents a $C_{1-10}$ alkyl group which may have a substituent, a $C_{1-10}$ alkoxy group which may have a substituent, a $C_{1-10}$ alkylthio group which may have a substituent, a $C_{2-10}$ alkenyl group which may have a substituent, a $C_{2-10}$ alkynyl group which may have a substituent, a 5-membered ring group which may have a substituent, or a $C_{6-12}$ aryl group which may have a substituent.

The organic cation transporter 3 (OCT3) inhibitor inhibits an activity of the OCT3. The OCT3 activity-inhibiting function can be measured by a method described in Examples.

The pharmaceutically acceptable salt indicates a derivative of the disclosed compound, modified by forming an acidic or basic salt of a parent compound. Examples of the pharmaceutically acceptable salt are not limited to, but include an inorganic acid salt of a basic residue such as amine and an organic acid salt thereof, and an alkali salt of an acidic residue such as carboxylic acid and an organic salt thereof. Examples of the pharmaceutically acceptable salt include a normal nontoxic salt of the parent compound and a quaternary ammonium salt thereof, generated from a nontoxic inorganic or organic acid. Such a normal nontoxic salt includes a salt derived from an inorganic acid and a salt prepared from an organic acid. Examples of the inorganic acid include hydrochloric acid, hydrobromic acid, sulfuric acid, sulfamic acid, phosphoric acid, and nitric acid. Examples of the organic acid include acetic acid, propionic acid, succinic acid, glycolic acid, stearic acid, lactic acid, malic acid, tartaric acid, citric acid, ascorbic acid, pamoic acid, maleic acid, hydroxymaleic acid, phenylacetic acid, glutamic acid, benzoic acid, salicylic acid, sulfanilic acid, 2-acetoxy benzoic acid, fumaric acid, toluenesulfonic acid, methanesulfonic acid, ethanedisulfonic acid, oxalic acid, and isethionic acid.

The pharmaceutically acceptable salt of the compound provided herein is synthesized by a usual chemical method from the parent compound containing a basic or acidic moiety. In general, for example, such salts are prepared by causing these compounds in a form of a free acid or a free base to react with a base or an acid in an appropriate stoichiometric amount in water, an organic solvent, or a mixture of these two kinds of solvents. In general, a non-aqueous medium such as ether, ethyl acetate, ethanol, isopropanol, or acetonitrile is preferable. Suitable salts are listed in "Remington's Pharmaceutical Sciences", 17th ed., Mack Publishing Company, Easton, Pa., 1985, p. 1418. Its disclosure is incorporated here by reference.

In the pharmaceutically acceptable solvate, a solvent is solvated to a target compound. An example of solvation is hydration. The compound of the present invention includes a compound containing a hydroxyl group, an amide group, or the like, which can form a hydrate with water in the atmosphere.

The "$C_{1-10}$ alkyl group which may have a substituent" is a $C_{1-10}$ alkyl group having one or more substituents selected from the following substituent group A. The $C_{1-10}$ alkyl group in the $C_{1-10}$ alkyl group which may have a substituent is a linear alkyl group having 1 to 10 carbon atoms, a branched alkyl group having 3 to 10 carbon atoms, or a cyclic alkyl group having 3 to 10 carbon atoms. Examples of the linear alkyl group include a methyl group, an ethyl group, a propyl group, a butyl group, a pentyl group, a hexyl group, a heptyl group, an octyl group, a nonyl group, and a decyl group. Examples of the branched alkyl group include an isopropyl group, an isobutyl group, a 1-methylpropyl group, a t-butyl group, a 1-methylbutyl group, a 2-methylbutyl group, a 3-methylbutyl group, a 1-ethylpropyl group, a 1,1-dimethylpropyl group, a 2,2-dimethylpropyl group, a 1,2-dimethylpropyl group, a 1-methylpentyl group, a 2-methylpentyl group, a 3-methylpentyl group, a 4-methylpentyl group, a 1-ethylbutyl group, a 2-ethylbutyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 5-methylhexyl group, a 3-ethylpentyl group, a 1-propylbutyl group, a 1,4-dimethylpentyl group, a 3,4-dimethylpentyl group, a 1,2,3-trimethylbutyl group, a 1-isopropylbutyl group, a 4,4-dimethylpentyl group, a 5-methylpentyl group, a 6-methylheptyl group, a 4-ethylhexyl group, a 2-propylpentyl group, a 2,5-dimethylhexyl group, a 4,5-dimethylhexyl group, a 2-ethyl-3-methylpentyl group, a 1,2,4-trimethylpentyl group, a 2-methyl-1-isopropylbutyl group, a 3-methyloctyl group, a 2,5-dimethylheptyl group, a 1-(1-methylpropyl)-2-methylbutyl group, a 1,4,5-trimethylhexyl group, a 1,2,3,4-tetramethylpentyl group, a 7-methyloctyl group, a 6-methylnonyl group, 8-methylnonyl group, a 5-ethyl-2-methylheptyl group, a 2,3-dimethyl-1-(1-methylpropyl) butyl group, a cyclopropylmethyl group, a 2-(cyclopropyl) ethyl group, a 3,7-dimethyloctyl group, a 3-(cyclobutyl) pentyl group, a cyclopentylmethyl group, and a cyclohexylmethyl group. Examples of the cyclic alkyl group include a cyclopropyl group, a cyclobutyl group, a cyclopentyl group, a cyclohexyl group, a cycloheptyl group, and a cyclooctyl group. In the $C_{1-10}$ alkyl group, a $C_{1-6}$ alkyl group is preferable, and a $C_{1-3}$ alkyl group is more preferable. Examples of the $C_{1-6}$ alkyl group include a methyl group, an ethyl group, a n-propyl group, an isopropyl group, a n-butyl group, an isobutyl group, a sec-butyl group, a tert-butyl group, a n-pentyl group, an isopentyl group, a neopentyl group, a tert-pentyl group, a 1-methylbutyl group, a 2-methylbutyl group, a 1,2-dimethylpropyl group, a 1-ethylpropyl group, a n-hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1-ethylbutyl group, a 1,1,2-trimethylpropyl group, a 1,2,2-trimethylpropyl group, a 1-ethyl-2-methylpropyl group, and a 1-ethyl-1-methylpropyl group.

The "$C_{1-10}$ alkoxy group which may have a substituent" is a $C_{1-10}$ alkoxy group having one or more substituents selected from the following substituent group A. Examples of the $C_{1-10}$ alkoxy group in the $C_{1-10}$ alkoxy group which may have a substituent include a group in which a group represented by —O— is bonded to an end of the above-described $C_{1-10}$ alkyl group. Specific examples thereof include a methoxy group, an ethoxy group, and a propyloxy group.

The "$C_{1-10}$ alkylthio group which may have a substituent" is a $C_{1-10}$ alkylthio group having one or more substituents selected from the following substituent group A. Examples of the $C_{1-10}$ alkylthio group in the $C_{1-10}$ alkylthio group which may have a substituent include a group in which a group represented by —S— is bonded to an end of the above-described $C_{1-10}$ alkyl group.

The "$C_{2-10}$ alkenyl group which may have a substituent" is a $C_{2-10}$ alkenyl group having one or more substituents selected from the following substituent group A. The $C_{2-10}$ alkenyl group in the $C_{2-10}$ alkenyl group which may have a substituent is a linear alkenyl group having 2 to 10 carbon atoms and at least one double bond, a branched alkenyl group having 3 to 10 carbon atoms, or a cyclic alkenyl group having 5 to 10 carbon atoms. Examples thereof include a vinyl group, an allyl group, a 3-butenyl group, a 4-pentenyl group, a 5-hexenyl group, a 6-heptenyl group, a 7-octenyl group, a 8-nonenyl (noneyl) group, a 9-decenyl group, a 1-methyl-2-butenyl group, a 2-methyl-2-butenyl group, a 2-methyl-3-butenyl group, a 2-pentenyl group, a 2-methyl-2-hexenyl group, and a 2-cyclopentenyl group. In the $C_{2-10}$ alkenyl group, a $C_{2-6}$ alkenyl group is preferable, and a $C_{2-3}$ alkenyl group is more preferable.

The "$C_{2-10}$ alkynyl group which may have a substituent" is a $C_{2-10}$ alkynyl group having one or more substituents selected from the following substituent group A. The alkynyl group is a monovalent group having at least one triple bond (two adjacent SP carbon atoms). Examples of the $C_{2-10}$ alkynyl group include an ethynyl group, a 1-propynyl group, a propargyl group, and a 3-butynyl group. The $C_{2-10}$ alkynyl group is preferably a $C_{2-6}$ alkynyl group, more preferably a $C_{2-5}$ alkynyl group, still more preferably a $C_{2-4}$ alkynyl group, and further still more preferably a $C_{2-3}$ alkynyl group.

The "$C_{6-12}$ aryl group which may have a substituent" is a $C_{6-12}$ aryl group having one or more substituents selected from the following substituent group A. The $C_{6-12}$ aryl group may be a heteroaryl group. The $C_{6-12}$ aryl group in the $C_{6-12}$ aryl group which may have a substituent group is an aromatic carbocyclic group or an aromatic heterocyclic group. Examples of the aromatic carbocyclic group and the aromatic heterocyclic group as the $C_{6-12}$ aryl group include a phenyl group, a 2-fluorophenyl group, a 3-fluorophenyl group, a 4-fluorophenyl group, a 4-chlorophenyl group, a 3,4-difluorophenyl group, a 2,4-difluorophenyl group, a 2-trifluoromethylphenyl group, a 3-trifluorophenylmethyl group, a 4-trifluoromethylphenyl group, a 4-methoxyphenyl group, a 4-methanesulfonylphenyl group, a 3-fluoro-4-methoxyphenyl group, a naphthyl group, a pyridinyl group, a 3-trifluoromethylpyridin-6-yl group, a 2-trifluoromethylpyridin-5-yl group, a 2-fluoropyridin-5-yl group, a 3-fluoropyridin-6-yl group, a 3-chloropyridin-6-yl group, a 2-methoxypyridin-5-yl group, a 3-methoxypyridin-6-yl group, a 2-difluoromethoxypyridin-5-yl group, a 3-difluoromethoxypyridin-6-yl group, a 2-pyrazinyl group, a 2-pyrimidinyl group, a 5-trifluoromethylpyrimidin-2-yl group, a 2-trifluoromethylpyrimidin-5-yl group, a 3-trifluoromethyl-6-pyridinyl group, a 3-pyridazinyl group, a pyrrol-1-yl group, a 2-imidazolyl group, a 1-imidazolyl group, a triazolyl group, a 3-isoxazolyl group, a 1,3,4-oxadiazol-2-yl group, a 5-methyl-1,3,4-oxadiazol-2-yl group, a 2-thiazolyl group, a thiadiazolyl group, a tetrazolyl group, a 2-methylpyridin-5-yl group, a 3-methylpyridin-6-yl group, a 2-difluoromethylpyridin-5-yl group, a 3-difluoromethylpyridin-6-yl group, a 2-trifluoromethoxypyridin-5-yl group, and a 3-trifluoromethoxypyridin-6-yl group.

Substituent Group A

A halogen atom, a cyano group, a hydroxyl group, an amino group, a nitro group, a $C_{1-6}$ alkyl group, a $C_{3-6}$ cycloalkyl group, a $C_{1-6}$ alkyl group which may be substituted with a fluorine atom, a $C_{1-6}$ alkyl group which may be substituted with a hydroxyl group, a $C_{1-6}$ alkyloxy group which may be substituted with a fluorine atom, a mono $C_{1-6}$ alkylamino group, a di $C_{1-6}$ alkylamino group, a $C_{1-6}$ alkyloxy $C_{1-6}$ alkyl group, a $C_{1-6}$ alkyloxycarbonyl group, a ($C_{1-6}$ alkyloxycarbonyl)amino group, a ($C_{1-6}$ alkyloxycarbonyl) $C_{1-6}$ alkylamino group, a $C_{1-6}$ alkylcarbonyl group, a $C_{1-6}$ alkylcarbonyloxy group, a $C_{1-6}$ alkylcarbonylamino group, a ($C_{1-6}$ alkylcarbonyl)$C_{1-6}$ alkylamino group, a mono $C_{1-6}$ alkylcarbamoyl group, a di $C_{1-6}$ alkylcarbamoyl group, a mono $C_{1-6}$ alkylcarbamoylamino group, a di $C_{1-6}$ alkylcarbamoylamino group, a (mono $C_{1-6}$ alkylcarbamoyl)$C_{1-6}$ alkylamino group, a (di $C_{1-6}$ alkyl carbamoyl)$C_{1-6}$ alkylamino group, a mono $C_{1-6}$ alkylcarbamoyloxy group, a di $C_{1-6}$ alkylcarbamoyloxy group, a $C_{1-6}$ alkylsulfonyl group, a $C_{1-6}$ alkylsulfonylamino group, a $C_{1-6}$ alkylsulfonyl ($C_{1-6}$ alkyl)amino group, a mono $C_{1-6}$ alkylsulfamoyl group, a di $C_{1-6}$ alkylsulfamoyl group, a (mono $C_{1-6}$ alkylsulfamoyl) amino group, a (di $C_{1-6}$ alkylsulfamoyl)amino group, a mono $C_{1-6}$ alkylsulfamoyl ($C_{1-6}$ alkyl)amino group, a di $C_{1-6}$ alkylsulfamoyl ($C_{1-6}$ alkyl)amino group, a 3 to 8-membered heterocycloalkyl group, an aromatic carbocyclic group, and an aromatic heterocyclic group.

Examples of the halogen atom include a fluorine atom, a chlorine atom, a bromine atom, and an iodine atom.

The "$C_{3-6}$ cycloalkyl group" is a cycloalkyl group having 3 to 6 carbon atoms, and specific examples thereof include a cyclopropyl group, a cyclobutyl group, a cyclopentyl group, and a cyclohexyl group.

The "$C_{1-6}$ alkyl group which may be substituted with a fluorine atom" includes a $C_{1-6}$ alkyl group and a $C_{1-6}$ alkyl group in which some or all of the hydrogen atoms in the $C_{1-6}$ alkyl group are substituted with fluorine atoms. Specific examples of the latter $C_{1-6}$ alkyl group substituted with fluorine atoms include a fluoromethyl group, a difluoromethyl group, a trifluoromethyl group, and a 1,2-difluoroethyl group.

The "$C_{1-6}$ alkyl group which may be substituted with a hydroxyl group" includes a $C_{1-6}$ alkyl group and a $C_{1-6}$ alkyl group in which some of the hydrogen atoms in the $C_{1-6}$ alkyl group are substituted with hydroxyl groups. Specific examples of the latter $C_{1-6}$ alkyl group substituted with hydroxyl groups include a hydroxymethyl group, a 2-hydroxyethyl group, and a 3-hydroxypropyl group.

The "$C_{1-6}$ alkyloxy group which may be substituted with a fluorine atom" includes a group in which a $C_{1-6}$ alkyl group or a $C_{1-6}$ alkyl group substituted with a fluorine atom is bonded to an oxygen atom. Specific examples of the $C_{1-6}$ alkyloxy group include a methoxy group, an ethoxy group, a n-propyloxy group, an isopropyloxy group, a n-butyloxy group, an isobutoxy group, a tert-butoxy group, and a n-pentyloxy group. Specific examples of the $C_{1-6}$ alkyloxy group substituted with a fluorine atom include a fluoromethoxy group, a difluoromethoxy group, a trifluoromethoxy group, and a 1,2-difluoroethoxy group.

The "mono $C_{1-6}$ alkylamino group" is a group in which one hydrogen atom in an amino group is substituted with a $C_{1-6}$ alkyl group. Specific examples thereof include a methylamino group, an ethylamino group, a n-propylamino group, an isopropylamino group, a n-butylamino group, a sec-butylamino group, and a tert-butylamino group.

The "di $C_{1-6}$ alkylamino group" is a group in which two hydrogen atoms in an amino group are substituted with $C_{1-6}$ alkyl groups. Specific examples thereof include a dimethylamino group, a diethylamino group, an ethylmethylamino group, a di (n-propyl)amino group, a methylpropylamino group, and a diisopropylamino group.

The "$C_{1-6}$ alkyloxy $C_{1-6}$ alkyl group" is a group in which one hydrogen atom in a $C_{1-6}$ alkyl group is substituted with a $C_{1-6}$ alkyloxy group. Specific examples thereof include a methoxymethyl group, an ethoxymethyl group, a n-propyloxymethyl group, an ethoxymethyl group, and an ethoxyethyl group.

The "$C_{1-6}$ alkyloxycarbonyl group" is a group in which a $C_{1-6}$ alkyloxy group is bonded to a carbonyl group. Specific examples thereof include a methoxycarbonyl group, an ethoxycarbonyl group, a n-propyloxycarbonyl group, an isopropyloxycarbonyl group, a n-butyloxycarbonyl group, an isobutoxycarbonyl group, a tert-butoxycarbonyl group, and a n-pentyloxycarbonyl group.

The "($C_{1-6}$ alkyloxycarbonyl)amino group" is a group in which a $C_{1-6}$ alkyloxycarbonyl group is bonded to an amino group. Specific examples thereof include a methoxycarbonylamino group, an ethoxycarbonylamino group, a n-propyloxycarbonylamino group, an isopropyloxycarbonylamino group, a n-butoxycarbonylamino group, an isobutoxycarbonylamino group, a tert-butoxycarbonylamino group, and a n-pentyloxycarbonylamino group.

The "($C_{1-6}$ alkyloxycarbonyl)$C_{1-6}$ alkyl amino group" is a group in which a hydrogen atom bonded to a nitrogen atom in a mono $C_{1-6}$ alkylamino group is substituted with a $C_{1-6}$ alkyloxycarbonyl group. Specific examples thereof include a (methoxycarbonyl)methylamino group, an (ethoxycarbonyl)methylamino group, and a (n-propyloxycarbonyl)methylamino group.

The "$C_{1-6}$ alkylcarbonyl group" is a group in which a $C_{1-6}$ alkyl group is bonded to a carbonyl group. Specific examples thereof include an acetyl group, a propionyl group, a butyryl group, an isobutyryl group, a valeryl group, an isovaleryl group, and a pivaloyl group.

The "$C_{1-6}$ alkylcarbonyloxy group" is a group in which a $C_{1-6}$ alkylcarbonyl group is bonded to an oxygen atom. Specific examples thereof include an acetoxy group, a propionyloxy group, a valeryloxy group, an isovaleryloxy group, and a pivaloyloxy group.

The "$C_{1-6}$ alkylcarbonylamino group" is a group in which one hydrogen atom in an amino group is substituted with a $C_{1-6}$ alkylcarbonyl group. Specific examples thereof include an acetamide group, a propionylamino group, an isobutyrylamino group, a valerylamino group, an isovalerylamino group, and a pivaloylamino group.

The "($C_{1-6}$ alkylcarbonyl)$C_{1-6}$ alkylamino group" is a group in which a hydrogen atom bonded to a nitrogen atom in a mono $C_{1-6}$ alkylamino group is substituted with a $C_{1-6}$ alkylcarbonyl group. Specific examples thereof include a (methylcarbonyl)methlyamino group, an (ethylcarbonyl)methylamino group, and a (n-propylcarbonyl)methylamino group.

The "mono $C_{1-6}$ alkylcarbamoyl group" is a group in which one hydrogen atom in a carbamoyl group is substituted with a $C_{1-6}$ alkyl group. Specific examples thereof include a methylcarbamoyl group, an ethylcarbamoyl group, a n-propylcarbamoyl group, an isopropylcarbamoyl group, a n-butylcarbamoyl group, a sec-butylcarbamoyl group, and a tert-butylcarbamoyl group.

The "di $C_{1-6}$ alkylcarbamoyl group" is a group in which two hydrogen atoms in a carbamoyl group are substituted with $C_{1-6}$ alkyl groups. Specific examples thereof include a dimethylcarbamoyl group, a diethylcarbamoyl group, an ethylmethylcarbamoyl group, a di (n-propyl)carbamoyl group, a methylpropylcarbamoyl group, and a diisopropylcarbamoyl group.

The "mono $C_{1-6}$ alkylcarbamoylamino group" is a group in which one hydrogen atom in an amino group is substituted with a $C_{1-6}$ alkylcarbamoyl group. Specific examples thereof include a methylcarbamoylamino group, an ethylcarbamoylamino group, a n-propylcarbamoylamino group, an isopropylcarbamoylamino group, a n-butylcarbamoylamino group, a sec-butylcarbamoylamino group, and a tert-butylcarbamoylamino group.

The "di $C_{1-6}$ alkylcarbamoylamino group" is a group in which one hydrogen atom in an amino group is substituted with a di $C_{1-6}$ alkylcarbamoyl group. Specific examples thereof include a dimethylcarbamoylamino group, a diethylcarbamoylamino group, a di (n-propyl)carbamoylamino group, a diisopropylcarbamoylamino group, a di (n-butyl) carbamoylamino group, a di (sec-butyl)carbamoylamino group, and a di (tert-butyl)carbamoylamino group.

The "(mono $C_{1-6}$ alkylcarbamoyl)$C_{1-6}$ alkylamino group" is a group in which a hydrogen atom bonded to a nitrogen atom in a mono $C_{1-6}$ alkylamino group is substituted with a mono $C_{1-6}$ alkylcarbamoyl group. Specific examples thereof include a (mono methylcarbamoyl)methlyamino group, a (mono ethylcarbamoyl)methylamino group, and a [mono (n-propyl)carbamoyl]methylamino group.

The "(di $C_{1-6}$ alkylcarbamoyl)$C_{1-6}$ alkylamino group" is a group in which a hydrogen atom bonded to a nitrogen atom in a mono $C_{1-6}$ alkylamino group is substituted with a di $C_{1-6}$ alkylcarbamoyl group. Specific examples thereof include a (dimethylcarbamoyl)methlyamino group, a (diethylcarbamoyl)methylamino group, and a [di(n-propyl)carbamoyl] methylamino group.

The "mono $C_{1-6}$ alkylcarbamoyloxy group" is a group in which a $C_{1-6}$ alkylcarbamoyl group is bonded to an oxygen atom. Specific examples thereof include a methylcarbamoyloxy group, an ethylcarbamoyloxy group, a n-propylcarbamoyloxy group, an isopropylcarbamoyloxy group, a n-butylcarbamoyloxy group, a sec-butylcarbamoyloxy group, and a tert-butylcarbamoyloxy group.

The "di $C_{1-6}$ alkylcarbamoyloxy group" is a group in which a di $C_{1-6}$ alkylcarbamoyl group is bonded to an oxygen atom. Specific examples thereof include a dimethylcarbamoyloxy group, a diethylcarbamoyloxy group, an ethylmethylcarbamoyloxy group, a di(n-propyl)carbamoyloxy group, a methylpropylcarbamoyloxy group, and a diisopropylcarbamoyloxy group.

The "$C_{1-6}$ alkylsulfonyl group" is a group in which a $C_{1-6}$ alkyl group is bonded to a sulfonyl group. Specific examples thereof include a methylsulfonyl group, an ethylsulfonyl group, a n-propylsulfonyl group, an isopropylsulfonyl group, a n-butylsulfonyl group, a sec-butylsulfonyl group, and a tert-butylsulfonyl group.

The "$C_{1-6}$ alkylsulfonylamino group" is a group in which one hydrogen atom in an amino group is substituted with a $C_{1-6}$ alkylsulfonyl group. Specific examples thereof include a methylsulfonylamino group, an ethylsulfonylamino group, a n-propylsulfonylamino group, an isopropylsulfonylamino group, a n-butylsulfonylamino group, a sec-butylsulfonylamino group, and a tert-butylsulfonylamino group.

The "$C_{1-6}$ alkylsulfonyl($C_{1-6}$ alkyl)amino group" is a group in which a hydrogen atom bonded to a nitrogen atom in a "$C_{1-6}$ alkylamino group" is substituted with a $C_{1-6}$ alkylsulfonyl group. Specific examples thereof include a methylsulfonyl(methyl)amino group, an ethylsulfonyl(methyl)amino group, and a (n-propyl)sulfonyl(methyl)amino group.

The "mono $C_{1-6}$ alkylsulfamoyl group" is a group in which a $C_{1-6}$ alkyl group is bonded to a sulfamoyl group. Specific examples thereof include a monomethylsulfamoyl group, a monoethylsulfamoyl group, a mono(n-propyl)sulfamoyl group, a monoisopropylsulfamoyl group, a mono(n-butyl)sulfamoyl group, a mono(sec-butyl)sulfamoyl group, and a mono(tert-butyl)sulfamoyl group.

The "di $C_{1-6}$ alkylsulfamoyl group" is a group in which a di $C_{1-6}$ alkyl group is bonded to a sulfamoyl group. Specific examples thereof include a dimethylsulfamoyl group, a diethylsulfamoyl group, a di(n-propyl)sulfamoyl group, a diisopropylsulfamoyl group, a di(n-butyl)sulfamoyl group, a di(sec-butyl)sulfamoyl group, and a di (tert-butyl)sulfamoyl group.

The "(mono $C_{1-6}$ alkylsulfamoyl)amino group" is a group in which one hydrogen atom in an amino group is substituted with a mono $C_{1-6}$ alkylsulfamoyl group. Specific examples thereof include a (monomethylsulfamoyl)amino group, a (monoethylsulfamoyl)amino group, a [mono(n-propyl)sulfamoyl]amino group, a (monoisopropylsulfamoyl)amino group, a [mono(n-butyl)sulfamoyl]amino group, a [mono (sec-butyl)sulfamoyl]amino group, and a (tert-butylsulfamoyl)amino group.

The "(di $C_{1-6}$ alkylsulfamoyl)amino group" is a group in which one hydrogen atom in an amino group is substituted with a di $C_{1-6}$ alkylsulfamoyl group. Specific examples thereof include a (dimethylsulfamoyl)amino group, a (diethylsulfamoyl)amino group, an (ethylmethylsulfamoyl)amino group, a [di(n-propyl)sulfamoyl]amino group, a (methylpropylsulfamoyl)amino group, and a (diisopropylsulfamoyl) amino group.

The "mono $C_{1-6}$ alkylsulfamoyl($C_{1-6}$ alkyl)amino group" is a group in which a hydrogen atom bonded to a nitrogen atom in a "mono $C_{1-6}$ alkylamino group" is substituted with a mono $C_{1-6}$ alkylsulfamoyl group. Specific examples thereof include a monomethylsulfamoyl(methly)amino group, a monoethylsulfamoyl(methyl)amino group, and a mono (n-propyl)sulfamoyl(methyl)amino group.

The "di $C_{1-6}$ alkylsulfamoyl($C_{1-6}$ alkyl)amino group" is a group in which a hydrogen atom bonded to a nitrogen atom in a "mono $C_{1-6}$ alkylamino group" is substituted with a di $C_{1-6}$ alkylsulfamoyl group. Specific examples thereof include a dimethylsulfamoyl(methly)amino group, a diethylsulfamoyl(methyl)amino group, and a di(n-propyl)sulfamoyl(methyl)amino group.

Examples of the "3 to 8-membered heterocycloalkyl group" include an azetidinyl group, a pyrrolidinyl group, a piperidinyl group, a piperazinyl group, an imidazolidinyl group, a tetrahydrofuranyl group, a tetrahydropyranyl group, a morpholinyl group, a 1-thia-4-azocyclohexyl group, and a 2,5-diazabicyclo[2.2.2]octanyl group.

Preferable Examples of the compound of the present invention as a first group are as follows. That is, a compound represented by formula (I), in which $R^1$, $R^2$, $R^3$, $R^5$, and $R^6$ each represent a hydrogen atom or a methyl group, and $R^4$ represents a group represented by formula (II). In this embodiment, $R^1$, $R^3$, $R^5$, and $R^6$ each preferably represent a hydrogen atom, and $R^2$ preferably represents a methyl group.

[Chemical Formula 15]

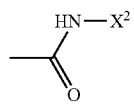

(II)

In formula (II), $X^2$ represents a group represented by —$Y^{21}$-$Y^{22}$-$Y^{23}$ or —$Y^{21}$-$Y^{22}$(—$Y^{23}Y^{24}$). $Y^{21}$ represents a linear or branched $C_{1-5}$ alkylene group. $Y^{22}$ represents a single bond, an oxygen atom, a sulfur atom, or a group represented by $SO_2$ (—S(=O)$_2$—).

$Y^{23}$ and $Y^{24}$ may be the same or different, and each represent:
a hydrogen atom;
a $C_{1-5}$ alkyl group;
a $C_{3-6}$ cycloalkyl group;
a pyrrolidinyl group which may be substituted with a methyl group, a group represented by =O (carbonyl group), or a halogen atom;
a thiazolidinyl group which may be substituted with a methyl group, a group represented by =O (carbonyl group), or a halogen atom;
a phenyl group bonded to a linear or branched $C_{1-5}$ alkyl group;
a phenyl group substituted with a $C_{1-5}$ alkoxy group bonded to a linear or branched $C_{1-5}$ alkyl group;
a pyrrolidinyl group substituted with a halogen atom, a nitro group, a $C_{1-5}$ alkyl group, $C_{1-5}$ alkoxy group, $C_{1-5}$ halgenoalkyl group, $C_{1-5}$ halgenoalkoxy group, a pyrrolidinyl group, or a group represented by =O (carbonyl group); or
a benzimidazolyl (benzomidazolyl) group.

In formula (II), $X^2$ may represent a group represented by —$Y^{25}(Y^{26})$-$Y^{27}$.

$Y^{25}$ represents a phenyl group in which one to three hydrogen atoms may be substituted with a halogen atom, a nitro group, a $C_{1-5}$ alkyl group, a $C_{1-5}$ alkoxy group, a $C_{1-5}$ halgenoalkyl group, a $C_{1-5}$ halgenoalkoxy group, a pyrrolidinyl group, or a group represented by =O.

$Y^{26}$ represents a pyrrolidinyl group which may substituted with a hydrogen atom, a phenyl group, a $C_{3-5}$ cycloalkyl group, or a $C_{1-5}$ alkyl group, or a pyrrole group which may be substituted with a $C_{1-5}$ alkyl group.

$Y^{27}$ represents:
a hydrogen atom;
a halogen atom;
a $C_{3-5}$ cycloalkyl group;
a pyrrolidinyl group bonded to a linear or branched $C_{1-5}$ alkyl group;
a piperidinyl group bonded to a linear or branched $C_{1-5}$ alkyl group;
a dioxolanyl group;
an imidazolyl (midazolyl) group;
a group represented by —C(=O)—$CH_3$;
a group represented by —C(=O)—$NH_2$;
a group represented by —C(=O)—$NC_5H_{10}$;
a group represented by —S($O_2$)$NHCH_3$;
a group represented by —S($O_2$)$NHC_3H_7$;
a group represented by —NC(=O)$OCH_3$;
a group represented by —NC(=O)$C_3H_5$;
a group represented by —NC(=O)$C_3H_7$; or
a group represented by

[Chemical Formula 16]

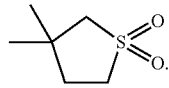

In preferable compounds of the first group, in formula (I), $R^1$, $R^2$, $R^3$, $R^5$ and $R^6$ each represent a hydrogen atom or a methyl group, and $R^4$ represents a group represented by formula (II). In formula (II), $X^2$ represents any of the groups represented by the following formulae (1-1) to (1-26). In this embodiment, $R^1$, $R^3$, $R^5$, and $R^6$ each preferably represent a hydrogen atom, and $R^2$ preferably represents a methyl group. Note that, in formulae (1-5), (1-8), (1-9), (1-10), (1-12), (1-14), (1-19), (1-22), (1-24), and (1-25), a bonding site is clearly indicated by giving a symbol (*) to a bonding portion to a nitrogen atom (N) adjacent to $X^2$.

[Chemical Formula 17]

(1)

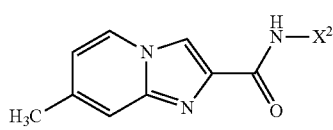

(1-1)

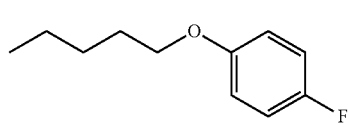

(1-2)

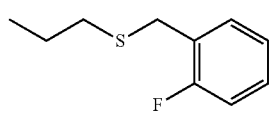

(1-3)

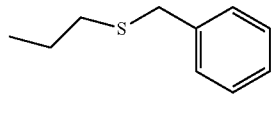

(1-4)

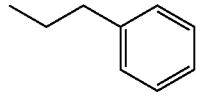

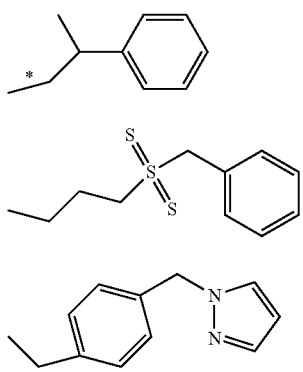
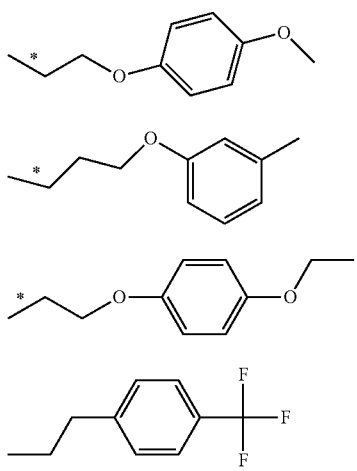
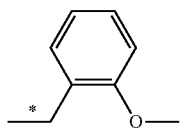
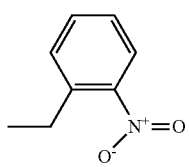
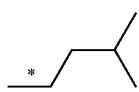
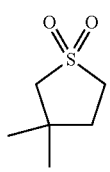
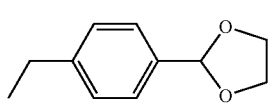
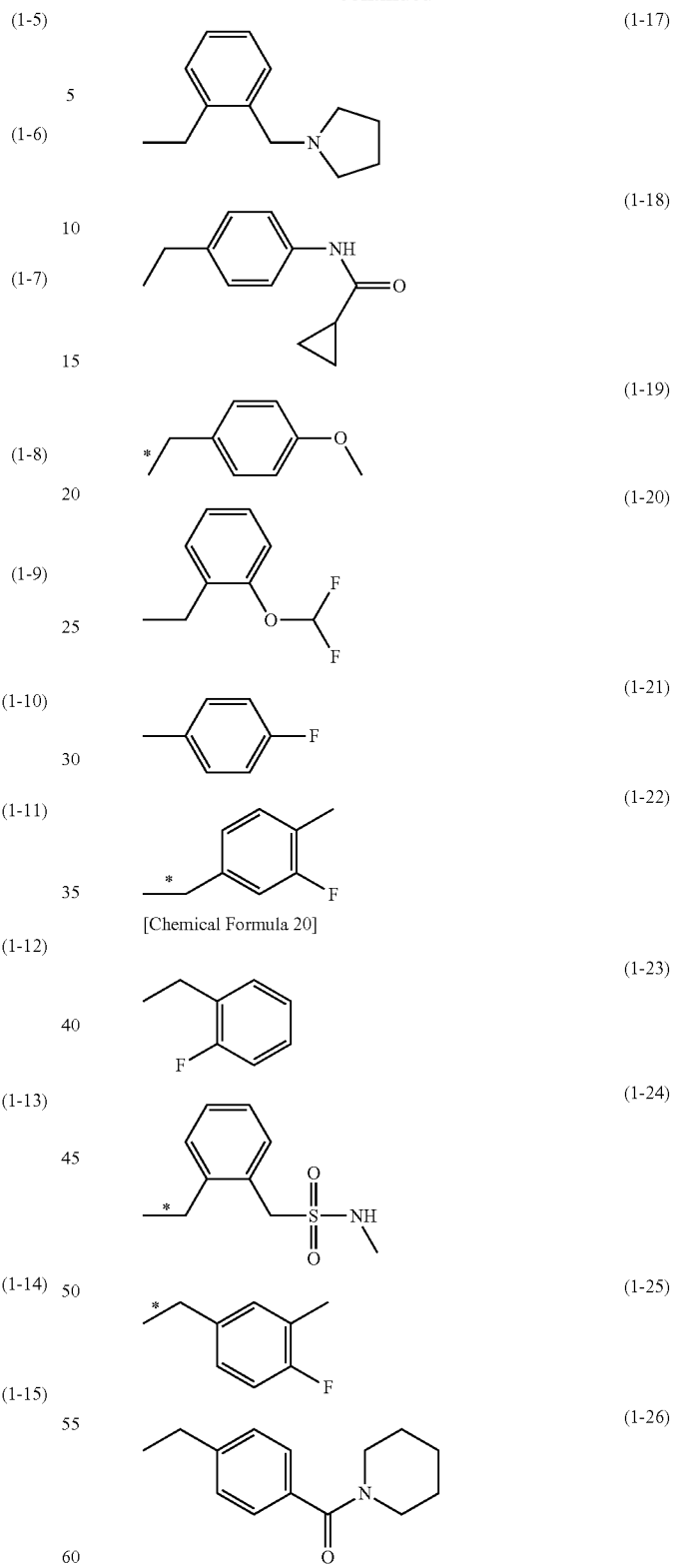
In a second group of the compound of the present invention, $R^1$, $R^2$, $R^3$, $R^5$ and $R^6$ each represent a hydrogen atom or a methyl group, and $R^4$ represents a group represented by formula (III). In formula (III), $X^3$ represents a group represented by the following formula (2-1) or (2-2). In this embodiment, $R^1$, $R^3$, $R^5$, and $R^6$ each preferably represent a hydrogen atom, and $R^2$ preferably represents a methyl group.

[Chemical Formula 21]

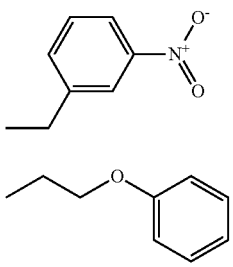

(2-1)

(2-2)

In a third group of the compound of the present invention, in formula (I), $R^1$, $R^2$, $R^3$, $R^5$ and $R^6$ each represent a hydrogen atom or a methyl group, and $R^4$ represents a group represented by formula (IV). In formula (IV), $X^4$ represents any of the groups represented by the following formulae (3-1) to (3-4). In this embodiment, $R^1$, $R^3$, $R^5$, and $R^6$ each preferably represent a hydrogen atom, and $R^2$ preferably represents a methyl group.

[Chemical Formula 22]

(3-1)

(3-2)

(3-3)

(3-4)

In a fourth group of the compound of the present invention, in formula (I), $R^1$, $R^2$, $R^3$, $R^5$ and $R^6$ each represent a hydrogen atom or a methyl group, and $R^4$ represents a group represented by formula (V). In formula (V), $X^5$ represents any of the groups represented by the following formulae (4-1), (5-1), (5-2), and (6-1).

In this embodiment, the following compounds are preferable. That is:

a compound in which $R^1$ represents a methyl group, $R^2$, $R^3$, $R^5$, and $R^6$ each represent a hydrogen atom, and $X^5$ represents a group represented by formula (4-1) in formula (V);

a compound in which $R^1$, $R^2$, $R^5$, and $R^6$ each represent a hydrogen atom, $R^3$ represents a methyl group, and $X^5$ represents a group represented by formula (5-1) or (5-2) in formula (V); or a compound in which $R^1$, $R^2$, $R^3$, $R^5$, and $R^6$ each represent a hydrogen atom, and $X^5$ represents any of the groups represented by formula (6-1) in formula (V). Note that, in formulae (4-1), (5-2), and (6-1), a bonding site is clearly indicated by giving a symbol (*) to a bonding portion to a sulfur atom (S) adjacent to $X^5$.

[Chemical Formula 23]

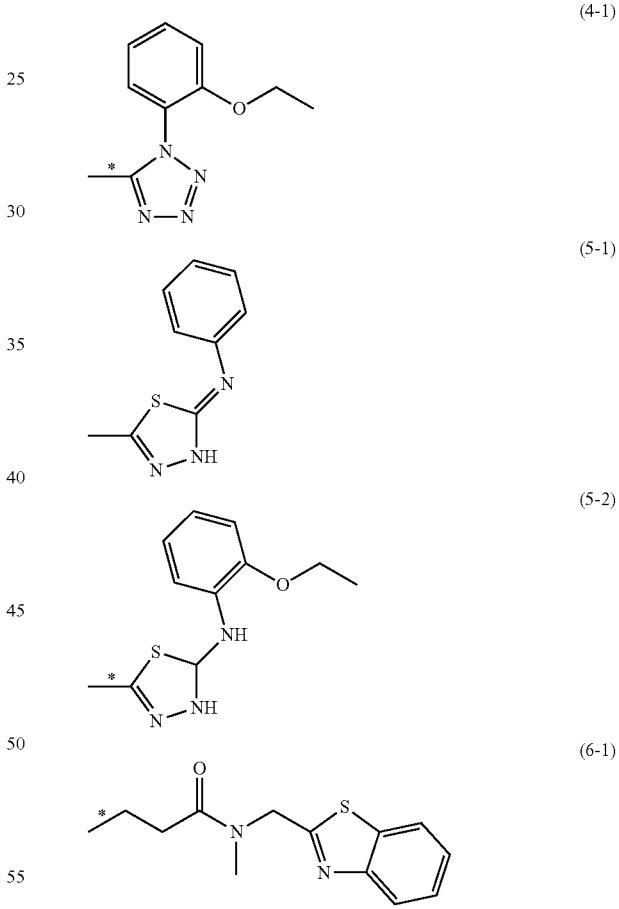

(4-1)

(5-1)

(5-2)

(6-1)

In a fifth group of the compound of the present invention, in formula (I), $R^1$, $R^2$, $R^3$, $R^5$ and $R^6$ each represent a hydrogen atom or a methyl group, and $R^4$ represents a group represented by formula (VI). In formula (VI), $X^6$ represents any of groups represented by the following formula (7-1) or (7-4). In this embodiment, $R^1$, $R^2$, $R^3$, $R^5$ and $R^6$ each preferably represent a hydrogen atom. Note that, in formula (7-4), a bonding site is clearly indicated by giving a symbol (*) to a bonding portion to a carbon atom (C) adjacent to $X^6$.

[Chemical Formula 24]

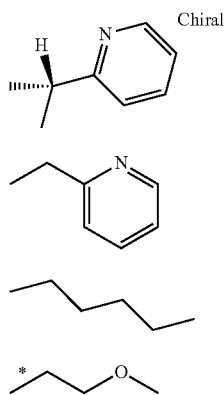

(7-1)

(7-2)

(7-3)

(7-4)

The above-described formula (7-1) includes stereoisomers, which are included in the compound of the present invention.

In a sixth group of the compound of the present invention, in formula (I), $R^1$, $R^2$, $R^3$, $R^5$ and $R^6$ each represent a hydrogen atom or a methyl group, and $R^4$ represents a group represented by formula (VII). In formula (VII), $X^7$ represents any of groups represented by the following formula (8-1) or (8-2). In this embodiment, $R^1$, $R^2$, $R^3$, $R^5$ and $R^6$ each preferably represent a hydrogen atom.

[Chemical Formula 25]

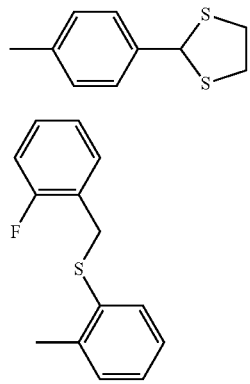

(8-1)

(8-2)

An OCT3 activity inhibitor including the compound of the present invention can be manufactured in a similar manner to a method disclosed in Re-publication of PCT International Publication No. 2005/084707. Examples of the activity of the OCT3 include a transport activity of dopamine, serotonin, noradrenaline, dopamine neurotoxin MPP+, a stimulant, or the like. These activities can be measured by a method well known to a person skilled in the art.

The OCT3 activity inhibitor including the compound of the present invention is effective in a treatment of a disease (depression and symptoms suggesting depression) relating to the OCT3. As described below, it has been demonstrated that depression and symptoms suggesting depression can be treated by inhibiting the organic cation transporter OCT3. For example, the prior literature (Kitaichi. et al., Neurosci Lett. 2005 Jul. 1-8; 382 (1-2): 195-200) reports that an antidepressant effect is exhibited in a forced swimming test by suppressing expression of an OCT3 gene in a mouse with an antisense or knock-out technology. On the other hand, the present OCT3 inhibitor is presumed to have an effect similar to suppressing the expression of the OCT3 gene because this OCT3 inhibitor inhibits a function of OCT3 protein.

As demonstrated in Examples, the compound of the present invention, a pharmaceutically acceptable salt thereof, or a pharmaceutically acceptable solvate thereof has the OCT3 inhibitory activity. Therefore, the present invention also provides a therapeutic agent for depression and symptoms suggesting depression, containing the above-described OCT3 inhibitor as an active component. The depression and symptoms suggesting depression include physical depression, unipolar depression, psychogenic functional disease, atypical depression, dysthymia, bipolar affective disease, seasonal depression, and persistent mood disorder.

The compound of the present invention can be administered orally or parenterally, and can be formulated in a form suitable for administration thereof. In order to use the compound of the present invention clinically, it is also possible to administer the compound after the compound is variously formulated by adding a pharmaceutically acceptable carrier according to an administration form thereof. As the carrier in this case, various additives in the related art of the pharmaceutical field can be used. Examples thereof include gelatin, lactose, sucrose, titanium oxide, starch, crystalline cellulose, hydroxypropylmethyl cellulose, carboxymethyl cellulose, corn starch, microcrystalline wax, white petrolatum, magnesium metasilicate aluminate, calcium phosphate anhydride, citric acid, trisodium citrate, hydroxypropyl cellulose, sorbitol, sorbitan fatty acid ester, polysorbate, sucrose fatty acid ester, polyoxyethylene, hardened castor oil, polyvinyl pyrrolidone, magnesium stearate, light anhydrous silicic acid, talc, vegetable oil, benzyl alcohol, gum arabic, propylene glycol, polyalkylene glycol, cyclodextrin, and hydroxypropyl cyclodextrin.

Examples of a dosage form to be formulated as a mixture of these carriers and the compound of the present invention include a tablet, a capsule, a granule, a solid preparation such as powder or a suppository, and a liquid preparation such as a syrup, an elixir, or an injection. These dosage forms can be prepared according to a method in the related art of the pharmaceutical field. Note that a liquid preparation may be dissolved or suspended in water or another appropriate medium when being used. Particularly, the injection may be dissolved or suspended in physiological saline or a glucose solution if necessary, and a buffer or a preservative may be further added thereto.

These preparations can contain the compound of the present invention in 1.0 to 100 wt %, preferably in 1.0 to 60 wt %, and can contain a pharmaceutically acceptable carrier in 0 to 99.0 wt %, preferably in 40 to 99.0 wt %, of the whole pharmaceutical composition.

When the compound of the present invention is used as a prophylactic or therapeutic agent for the above-described disease or illness, a dosage and a frequency of administration depend on a patient's sex, age, weight, a degree of symptoms, a type and a scope of a therapeutic effect to be aimed at, and the like. However, in general, for oral administration, 0.001 to 10 mg thereof is administered, preferably 0.01 to 2 mg is administered one to several times, to an adult per day and per kg of his/her weight. In addition, the compound of the present invention can be also prophylactically administered for some symptoms.

OCT3 Detection Agent Including Compound of Present Invention

An OCT3 detection agent including the compound of the present invention is for detecting whether OCT3 protein is included in biological tissues, cultured cells, artificial membranes, or the like in which an existing amount of the OCT3 protein is desired to be checked, or for obtaining an index of a content of the OCT3 protein. An aqueous solution of the detection agent including the compound of the present invention is added dropwise to biological tissues, cultured cells, artificial membranes, or the like in which an existing amount of the OCT3 protein is desired to be checked. Then, the compound of the present invention is bonded to the OCT3 protein, and therefore, a concentration of the compound of the present invention in the aqueous solution is reduced. That is, when the concentration of the compound of the present invention is measured, if the concentration of the compound of the present invention is reduced, it can be recognized that the OCT3 protein is present. An antibody against the OCT3 protein is commercially available, and can be used as a detection agent. However, the antibody is high molecular protein, and therefore, is sensitive to heat. Therefore, it is necessary to store the antibody at low temperature. In addition, the antibody is high molecular protein, and therefore, it is difficult to store the antibody for a long time, and manufacturing cost thereof is high. On the other hand, the compound of the present invention or the like is resistant to heat, can be stored for a long time at normal temperature, and can be relatively inexpensively manufactured by chemical synthesis.

Example 1

In order to measure an activity to inhibit substrate uptake by the OCT3 in each compound, a histamine uptake experiment was performed as follows.

A histamine uptake experiment was performed according to a method described in Br J Pharmacol. 2002; 136 (6): 829-836. In this experiment, HEK293 cells, which are human embryonic kidney cell lines expressing a human organic cation transporter 3 (hOCT3), were used. The HEK293 cells were seeded at $1.5 \times 10^5$ cells/well in a 24-well plate and cultured overnight in a carbon dioxide incubator. After being dissolved in a 100% DMSO solution, the test substance was dissolved in a HBSS-HEPES solution (a buffer solution adjusted to pH 7.4 with 1M sodium hydroxide, by dissolving 9.7 g of Hanks balanced salt, 25 mL of 1.4% sodium bicarbonate, and 25 mL of 1M HEPES in 940 mL of ultrapure water). After a cell culture medium was removed, a pretreatment for 5 minutes was performed with 1 mL of the HBSS-HEPES solution. Thereafter, the test substance and [3H]histamine (final concentration: 100 nM) were added to the cells and allowed to react for 1 minute at room temperature. After completion of the reaction, the reaction was stopped with the ice-cooled HBSS-HEPES solution, and extracellular fluid was aspirated by an aspirator. The cells were then washed two times with the HBSS-HEPES solution. After washing, the cells were lysed in a 0.5 M sodium hydroxide aqueous solution. An amount of histamine present in the cells was determined by measuring a radioactivity in the cell lysate with a liquid scintillation counter. A protein content of the cells was measured using the cell lysate by a Lowry method (J Biol Chem. 1951; 193 (1): 265-75). A Histamine uptake amount per protein content when there is no uptake inhibitor is regarded as 100% of a histamine uptake ratio (control), and the histamine uptake ratio (%) in the presence of 30 μM of the test substance was calculated. In addition, a value calculated by subtracting this histamine uptake ratio from 100(%) was regarded as an OCT3 inhibition ratio (%). Furthermore, an OCT3 inhibitory activity ($IC_{50}$ value) was calculated from suppression curves at the concentrations of $10^{-7}$ to $10^{-3}$ M of the test substance.

Calculation of Predicted Value of log P

Log P of each compound was calculated by inputting a structure of the compound to Marvin software (version 5.7.0), and was denoted in Tables. When the OCT3 inhibitor is used as a therapeutic agent for depression, intracerebral transferability becomes a problem. Many existing OCT3 inhibitors have a small log P value and bad intracerebral transferability. A compound having a large log P value was designed, and the log P value was shown together with the $IC_{50}$ value. Note that it is possible to predict the intracerebral transferability using this log P value.

A ratio of a brain concentration with respect to a blood concentration (hereinafter, expressed by Brain/Blood) was predicted from the structure of the compound, and also shown. A plurality of prediction methods has been reported. Brain/Blood was calculated based on Prabha et al., In Silico Modeling for Blood-Brain Barrier Permeability Predictions, Drug absorption studies, 2008, volume VII, 3, 510-556, using the following equation.

$$\log(\text{Brain/Blood}) = -0.0148 \times \text{PSA} + 0.152 \times \log P + 0.139$$

Note that PSA represents a polarity surface area, which was calculated using the above-described Marvin software.

The Brain/Blood value predicted with the above method was verified with an experiment using BALB/c mice. As test substances in the verification experiment, two compounds of SR-4277 and Famotidine were used. A strong OCT3 inhibitory effect of SR-4277 has been confirmed. Both the OCT3 inhibitory effect and an antidepressant effect of Famotidine have been confirmed. The test substance was administered in 5 mg/kg to the mice. The mice were anesthetized in advance with isoflurane, and exsanguination was performed from the vena cava of the mice five minutes after the administration. Brains were removed, and weights thereof were measured. After that, a brain homogenate was prepared. The collected blood was subjected to centrifugation, and plasma was thereby prepared. Concentrations of the test substance in plasma and the brain homogenate were measured with HPLC and MS. Results of the predicted value and the measured value of Brain/Blood are shown below.

TABLE 1

| Compound ID | Predicted value | | Predicted value | Measured value |
| --- | --- | --- | --- | --- |
| | logP | PSA | Brain/Blood | |
| SR-4277 | 3.3 | 46 | 0.90 | 1.10 |
| Famotidine | −1.9 | 176 | 0.002 | 0.10 |

When an experimental error in the verification experiment is taken into consideration, in the results of the verification experiment, the predicted value and the measured value are very close (close in order) to each other. It can be said that the prediction method of the above-described Brain/Blood value is very excellent in prediction accuracy. This method was also applied to other compounds, and Brain/Blood values thereof were calculated.

Log P values of the compounds were distributed between −0.2 and 4.6 as shown in the following Table (median 2.7). Therefore, it was predicted that fat solubility would be high and oral absorption would be good. The Brain/Blood values of the compounds were distributed between 0.08 and 1.72 as shown in the following Table (median 0.64). It was predicted that the brain concentration of the compound was almost the same as the blood concentration. Therefore, the compounds have not only the excellent OCT3 inhibitory activity but also excellent utility as an oral agent or a central drug. Many compounds better than famotidine in terms of the OCT3 inhibitory activity and the intracerebral transferability were obtained. It is confirmed that famotidine has the OCT3 inhibitory activity (Non-Patent Literature 2) and the antidepressant effect (Patent Literature 4). Utility in the treatment of depression or the like can be expected.

A chemical structure of X and the OCT3 inhibitory activity thereof are shown below.

TABLE 2

| Series | Common structure (expressed in a form of R—X: R is a common structure) |
|---|---|
| 1 | (structure image) |

| Series | Number | Compound ID | X (expressed in a form of —X: A symbol (*) is given to a bonding site in a compound in which a bonding portion to a nitrogen atom (N) adjacent to X is not clear.) | Histamine uptake ratio with respect to control (%) | OCT3 inhibition ratio (%) | Molecular weight | logP predicted value | Brain/Blood predicted value |
|---|---|---|---|---|---|---|---|---|
| 1 | 1 | SR-5410 | (structure) | 13.9 | 86.1 | 341 | 3.1 | 0.61 |
| 1 | 2 | SR-4277 | (structure) | 15.4 | 84.6 | 343 | 3.3 | 0.90 |
| 1 | 3 | SR-5301 | (structure) | 16.0 | 84 | 325 | 3.2 | 0.85 |
| 1 | 4 | SR-5349 | (structure) | 17.1 | 82.9 | 279 | 2.8 | 0.74 |
| 1 | 5 | SR-5351 | (structure) | 17.4 | 82.6 | 293 | 3.1 | 0.84 |
| 1 | 6 | SR-5315 | (structure) | 24.3 | 75.7 | 371 | 1.4 | 0.14 |
| 1 | 7 | SR-5402 | (structure) | 25.9 | 74.1 | 345 | 2.6 | 0.38 |
| 1 | 8 | SR-5406 | (structure) | 29.2 | 70.8 | 325 | 2.2 | 0.33 |
| 1 | 9 | SR-5381 | (structure) | 38.3 | 61.7 | 323 | 3.0 | 0.58 |

TABLE 2-continued

| | | | | | | | | |
|---|---|---|---|---|---|---|---|---|
| 1 | 10 | SR-5403 | (propoxy-phenyl-ethoxy) | 40.3 | 59.7 | 339 | 2.6 | 0.37 |
| 1 | 11 | SR-5405 | (propyl-phenyl-CF3) | 42.0 | 58 | 347 | 3.6 | 1.01 |
| 1 | 12 | SR-5355 | (methyl-methoxyphenyl) | 45.1 | 54.9 | 295 | 2.3 | 0.46 |
| 1 | 13 | SR-5354 | (ethyl-nitrophenyl) | 47.0 | 53 | 311 | 2.4 | 0.14 |
| 1 | 14 | SR-5370 | (isopentyl) | 52.2 | 47.8 | 245 | 2.3 | 0.64 |
| 1 | 15 | SR-5320 | (dimethyl sulfolane) | 55.0 | 45 | 307 | −0.2 | 0.08 |
| 1 | 16 | SR-5372 | (ethyl-phenyl-dioxolane) | 55.0 | 45 | 337 | 2.4 | 0.35 |
| 1 | 17 | SR-5326 | (ethyl-phenyl-CH2-pyrrolidine) | 56.9 | 43.1 | 348 | 2.8 | 0.68 |
| 1 | 18 | SR-5385 | (ethyl-phenyl-NH-C(O)-cyclopropyl) | 58.1 | 41.9 | 348 | 2.5 | 0.25 |
| 1 | 19 | SR-5333 | (methyl-methoxyphenyl) | 58.3 | 41.7 | 295 | 2.3 | 0.46 |
| 1 | 20 | SR-5400 | (ethyl-phenyl-OCHF2) | 59.2 | 40.8 | 331 | 3.2 | 0.64 |
| 1 | 21 | SR-5379 | (methyl-fluorophenyl) | 60.3 | 39.7 | 269 | 2.9 | 0.78 |

TABLE 2-continued

| | | | | Histamine uptake ratio with respect to control (%) | OCT3 inhibition ratio (%) | Molecular weight | logP predicted value | Brain/Blood predicted value |
|---|---|---|---|---|---|---|---|---|
| 1 | 22 | SR-5309 | 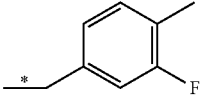 | 61.5 | 38.5 | 297 | 3.1 | 0.84 |
| 1 | 23 | SR-5310 | 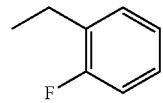 | 61.8 | 38.2 | 283 | 2.6 | 0.70 |
| 1 | 24 | SR-5408 | 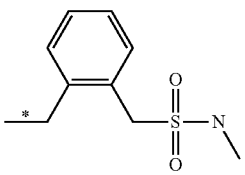 | 64.2 | 35.8 | 372 | 1.1 | 0.08 |
| 1 | 25 | SR-5308 | 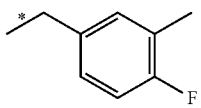 | 65.0 | 35 | 297 | 3.1 | 0.84 |
| 1 | 26 | SR-5380 | 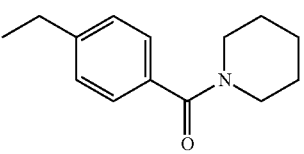 [SMILES: CCc1ccc(C(=O)N2CCCCC2)cc1] | 66.7 | 33.3 | 376 | 2.6 | 0.35 |

TABLE 3

| Series | Common structure (expressed in a form of R—X: R is a common structure) |
|---|---|
| 2 | 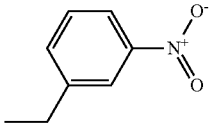 |

| Series | Number | Compound ID | X (expressed in a form of —X) | Histamine uptake ratio with respect to control (%) | OCT3 inhibition ratio (%) | Molecular weight | logP predicted value | Brain/Blood predicted value |
|---|---|---|---|---|---|---|---|---|
| 2 | 1 | SR-5335 | 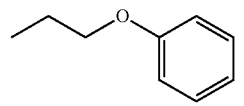 | 55.6 | 44.4 | 325 | 2.6 | 0.20 |
| 2 | 2 | SR-5414 |  | 56.4 | 43.6 | 309 | 2.6 | 0.69 |

TABLE 4

| Series | Common structure (expressed in a form of R—X: R is a common structure) |
|---|---|
| 3 | 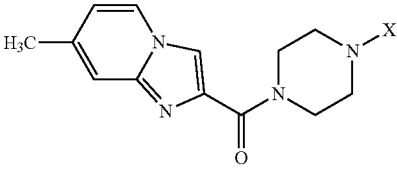 |

| Series | Number | Compound ID | X (expressed in a form of —X) | Histamine uptake ratio with respect to control (%) | OCT3 inhibition ratio (%) | Molecular weight | logP predicted value | Brain/Blood predicted value |
|---|---|---|---|---|---|---|---|---|
| 3 | 1 | SR-5340 |  | 41.6 | 58.4 | 334 | 2.5 | 0.83 |
| 3 | 2 | SR-5371 | 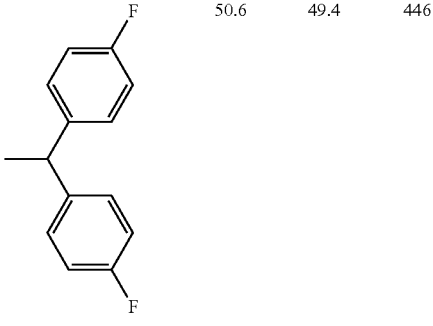 | 47.6 | 52.4 | 338 | 2.8 | 0.92 |
| 3 | 3 | SR-5344 | 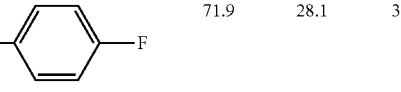 | 50.6 | 49.4 | 446 | 4.6 | 1.71 |
| 3 | 4 | SR-5364 | 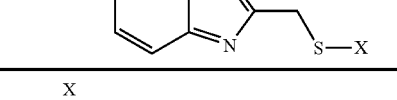 | 71.9 | 28.1 | 338 | 2.8 | 0.92 |

TABLE 5

| Series | Common structure (expressed in a form of R—X: R is a common structure) |
|---|---|
| 4 | 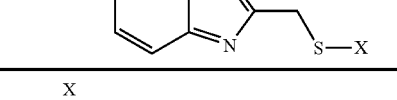 |

| Series | Number | Compound ID | X (expressed in a form of —X: A symbol (*) is given to a bonding site in a compound in which a bonding portion to a nitrogen atom (N) adjacent to X is not clear.) | Histamine uptake ratio with respect to control (%) | OCT3 inhibition ratio (%) | Molecular weight | logP predicted value | Brain/Blood predicted value |
|---|---|---|---|---|---|---|---|---|
| 4 | 1 | SR-4229 | 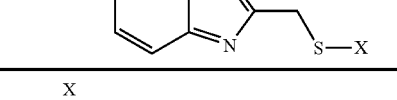 | 38.7 | 61.3 | 366 | 3.3 | 0.40 |

TABLE 6

| Series | Common structure (expressed in a form of R—X: R is a common structure) |
|---|---|
| 5 | 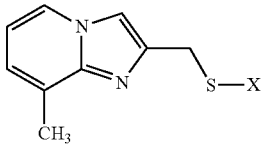 |

| Series | Number | Compound ID | X (expressed in a form of —X: A symbol (*) is given to a bonding site in a compound in which a bonding portion to a nitrogen atom (N) adjacent to X is not clear.) | Histamine uptake ratio with respect to control (%) | OCT3 inhibition ratio (%) | Molecular weight | logP predicted value | Brain/Blood predicted value |
|---|---|---|---|---|---|---|---|---|
| 5 | 1 | SR-4281 | 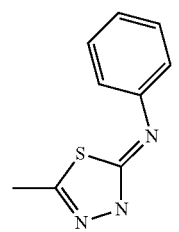 | 58.5 | 41.5 | 353 | 4.6 | 1.09 |
| 5 | 2 | SR-4233 | 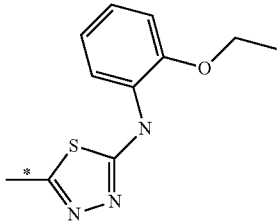 [SMILES: CCOc1ccccc1Nc1nnc(C)s1] | 72.6 | 27.4 | 397 | 4.2 | 0.66 |

TABLE 7

| Series | Common structure (expressed in a form of R—X: R is a common structure) |
|---|---|
| 6 | 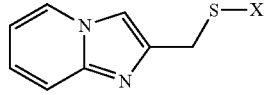 |

| Series | Number | Compound ID | X (expressed in a form of —X: A symbol (*) is given to a bonding site in a compound in which a bonding portion to a nitrogen atom (N) adjacent to X is not clear.) | Histamine uptake ratio with respect to control (%) | OCT3 inhibition ratio (%) | Molecular weight | logP predicted value | Brain/Blood predicted value |
|---|---|---|---|---|---|---|---|---|
| 6 | 1 | SR-4234 | 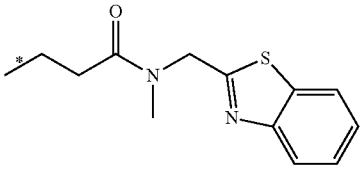 [SMILES: CCCC(=O)N(C)Cc1nc2ccccc2s1] | 66.7 | 33.3 | 396 | 2.7 | 0.63 |

TABLE 8

| Series | Common structure (expressed in a form of R—X: R is a common structure) |
|---|---|
| 7 | 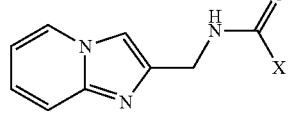 |

| Series | Number | Compound ID | X (expressed in a form of —X: A symbol (*) is given to a bonding site in a compound in which a bonding portion to a nitrogen atom (N) adjacent to X is not clear.) | Histamine uptake ratio with respect to control (%) | OCT3 inhibition ratio (%) | Molecular weight | logP predicted value | Brain/Blood predicted value |
|---|---|---|---|---|---|---|---|---|
| 7 | 1 | SR-4290 | Chiral | 47.9 | 52.1 | 388 | 3.1 | 0.54 |
| 7 | 2 | SR-4214 |  | 49.5 | 50.5 | 374 | 2.5 | 0.44 |
| 7 | 3 | SR-4207 |  | 54.8 | 45.2 | 353 | 3.7 | 1.05 |
| 7 | 4 | SR-4280 |  | 59.0 | 41 | 341 | 1.9 | 0.40 |

TABLE 9

| Series | Common structure (expressed in a form of R—X: R is a common structure) |
|---|---|
| 8 | 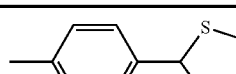 |

| Series | Number | Compound ID | X (expressed in a form of —X) | Histamine uptake ratio with respect to control (%) | OCT3 inhibition ratio (%) | Molecular weight | logP predicted value | Brain/Blood predicted value |
|---|---|---|---|---|---|---|---|---|
| 8 | 1 | SR-5327 |  | 54.5 | 45.5 | 355 | 2.7 | 0.73 |
| 8 | 2 | SR-5321 |  | 56.7 | 43.3 | 391 | 4.0 | 1.16 |

IC$_{50}$ values of some compounds and an IC$_{50}$ value of famotidine having the strong OCT3 inhibitory activity, measured simultaneously as a comparison are as follows.

TABLE 10

| Compound ID | OCT3 inhibitory activity, IC$_{50}$ value (μM) |
|---|---|
| SR-4277 | 8.2 |
| SR-4056 | 12.7 |
| SR-4229 | 25.3 |
| SR-4241 | 25.5 |
| SR-4272 | 27.2 |
| SR-4211 | 29.6 |
| SR-4061 | 30.8 |
| SR-4059 | 38.0 |
| SR-4074 | 48.8 |
| Famotidine | 67.6 |

Particularly, SR-4277 has IC$_{50}$ of 8.2 μM and IC$_{80}$ of 30 μM. SR-4277 has the strong inhibitory activity. Note that it is easily estimated that a compound having the OCT3 inhibitory activity has OCT1 and OCT2 inhibitory activities because the OCT3 is very similar to the OCT1 and the OCT2 in amino acid sequences.

The imidazopyridine derivative of the present invention is a strong OCT3 protein inhibitor, and is useful as an OCT3 detection agent.

When an imidazopyridine derivative aqueous solution is added dropwise to biological tissues, cultured cells, artificial membranes, or the like in which an existing amount of the OCT3 protein is desired to be checked, the imidazopyridine derivative is bonded to the OCT3 protein, and therefore, a concentration of the imidazopyridine derivative in the aqueous solution is reduced. When this concentration is reduced, it is understood that the OCT3 protein is present. As a specific example, a method for detecting the OCT3 protein can be realized by a histamine uptake experiment described below.

For example, a histamine uptake experiment is performed according to a method described in Br J Pharmacol. 2002; 136 (6): 829-836. An existing amount of the OCT3 protein can be estimated from an amount of a compound free in the extracellular fluid in a method similar to a method described in Japanese Patent No. 1936624. In the experiment, HEK293 cells, which are human embryonic kidney cell lines expressing the human organic cation transporter 3 (OCT3) are prepared as a positive control, and cell lines the OCT3 expression of which is desired to be checked are prepared as test cells. The cells are seeded at 1.5×10$^5$ cells/well in a 24-well plate and cultured overnight in a carbon dioxide incubator. After being dissolved in a 100% DMSO solution, the test substance was dissolved in a HBSS-HEPES solution (a buffer solution adjusted to pH 7.4 with 1M sodium hydroxide, by dissolving 9.7 g of Hanks balanced salt, 25 mL of 1.4% sodium bicarbonate, and 25 mL of 1M HEPES in 940 mL of ultrapure water). After a cell culture medium is removed, a pretreatment for 5 minutes is performed with 1 mL of the HBSS-HEPES solution. Thereafter, the compound of the present invention as the test substance and histamine (final concentration: 100 nM) are added to the cells and allowed to react for 1 minute at room temperature. After completion of the reaction, the reaction is stopped with the ice-cooled HBSS-HEPES solution, and extracellular fluid is collected.

By analyzing the collected extracellular fluid with LC/MS, it is possible to identify a concentration and an existing amount of the compound of the present invention in the extracellular fluid. In this way, by subtracting the amount of the compound in the collected extracellular fluid from the amount of the administered compound, it is possible to calculate an amount of the compound bonded to the OCT3, and it is possible to confirm presence of the OCT3 protein in the cell. Another method for estimating the concentration of the compound of the present invention in the extracellular fluid is as follows. Standard solutions of the compound of the present invention, having a plurality of concentrations, are prepared in advance, and absorbance thereof is measured in advance. Subsequently, the absorbance of the extracellular fluid collected in the above-described histamine uptake experiment is measured and compared with the measured value in the standard solution measured in advance. The concentration can be thereby easily estimated even without using the LC/MS.

An antibody against the OCT3 protein is commercially available, and can be used as a detection agent. However, the antibody is high molecular protein, and is sensitive to heat (stored at 4° C.). Therefore, it is difficult to store the antibody for a long time, and manufacturing cost thereof is high. On the other hand, the imidazopyridine derivative is resistant to heat, can be stored for a long time at normal temperature, and can be inexpensively manufactured by chemical synthesis.

Example 2

Example 2 relates to a method for evaluating an antidepressant effect and anti-symptoms suggesting depression. Currently, the most general method for evaluating the antidepressant effect is a forced swimming test developed by Porsolt et al. (Porsolt R D et al., Arch Int Pharmacodyn. 1977; 229: 327-336). In this forced swimming test, mice or rats as test animals are forced to swim in water tanks from which the mice or rats cannot escape. Then, an immobility behavior of the test animals after an escape behavior thereof (a state in which only the head is above the water surface and the test animals are floating without moving the hands or feet) is observed. When the test animals are put into the water tanks again 24 hours or more later, the immobility behavior is expressed earlier than in the first experiment. Duration of this immobility behavior for a certain time (usually about 5 minutes) is relatively accurately reproduced.

It is known that existing antidepressants clinical effectiveness of which has been recognized specifically and significantly suppress the duration of the immobility behavior induced in this forced swimming test. It is considered that the existing antidepressants are useful for detecting the antidepressant effect. Test operation of this method is extremely simple. Therefore, this method is widely used in pre-clinical evaluation of novel antidepressant candidates and phenotypic analysis of genetically modified animals (Minoru Tsuji et al., Japanese pharmacological magazine, v130, p 97-104, 2007).

The following method is usually used as a test design using this method. First, standard antidepressants (for example, tricyclic antidepressants) as a positive control drug, and a buffer solution etc. including no drug as a negative control, are administered respectively to different individual animals. The experimental conditions of the forced swimming test are set so as to be able to detect "a change in behavior specifically occurring".

Subsequently, a test substance is administered in a similar schedule to the positive control drug. When it is confirmed that a similar change in the behavior to the positive control drug occurs, it can be concluded that the test drug can be expected to have the antidepressant effect which is a similar clinical effect to that of the positive control drug (Yutaka Nakagawa, practice behavioral pharmacology, Kinpodo, 2010, p 35-42).

Note that consideration is required to be given in order to obtain a stable experimental result by constantly setting experimental conditions used in this test, such as weights of mice, a diameter of a cylindrical water tank, and a water depth in the water tank, to fixed values. In addition, it is known that expression time of the immobility behavior varies depending on water temperature in the water tank. Therefore, the water temperature throughout the test needs to be kept constant (usually about 24° C.). It is effective and popular to set high water temperature about 1.0 to 1.5° C. higher than room temperature (Yutaka Nakagawa, practice behavioral pharmacology, Kinpodo, 2010, p 35-42).

Furthermore, it is known that an apparent immobility behavior is suppressed even while a spontaneous movement activity is enhanced by administration of a central stimulant or the like. Therefore, in order to confirm the antidepressant effect surely, it is necessary to confirm not only suppression of the immobility behavior in the forced swimming test, but also no change in the spontaneous movement activity of animals by administration of an antidepressant candidate (Minoru Tsuji et al., Japanese pharmacological magazine, v130, p 97-104, 2007).

Example 3

Example 3 relates to confirmation of the antidepressant effect by the OCT3 inhibitor and a combined effect thereof with an antidepressant imipramine.

The confirmation of the antidepressant effect by the OCT3 inhibitor and the combined effect thereof with the antidepressant imipramine can be performed in a similar manner to a prior literature (Kitaichi. et al., Neurosci Lett. 2005 Jul. 1-8; 382 (1-2): 195-200). Specifically, a test is performed as follows.

In an experiment, ddY male mice each weighing 28 to 33 g (Japan SLC, Inc.) are used. The ddY mice are non-inbred mice, have high fertility, and grow well. The ddY mouse is a typical strain name for laboratory mice widely used in a variety of tests and research including tests for medicinal, pharmacology, toxicity, and the like. After being acquired, these mice are bred in a room in which temperature (22 to 24° C.), humidity (50 to 60%), and lighting (lighting 8:00 to 20:00) are controlled for three or more days. In the first forced swimming test, all the experimental mice are forced to swim in glass cylinders (diameter 15.5 cm, depth 17 cm, water depth 12 cm, water temperature 25° C.) for 300 seconds to measure immobility time. The mice are distributed into experimental groups (an OCT3 inhibitor-administrated group, a positive control group, and a negative control group) such that an average value of the immobility time is almost the same. At this time, mice expressing the immobility time having a difference of 60 seconds or more from the average value of the immobility time (long or short) are excluded from the experiment. In order to prevent pheromone or the like of the mice used in the test from affecting subsequent mice, water in the water tank is exchanged for each mouse. In the OCT3 inhibitor-administrated group, the OCT3 inhibitor which was dissolved the day after swimming in a physiological buffer solution (140 mM NaCl, 3.0 mM KCl, 1.5 mM NaH2PO4, 1.2 mM MgCl2, 1.2 mM CaCl2, pH 7.4) is continuously injected into the third cerebral ventricle with an osmotic pump based on a method of a previous report (J. Chem. Neuroanat. 2000 20: 375-87).

One week after the injection, the mice are forced to swim for 300 seconds again in the cylinders to measure the immobility time. In the positive control group, the antidepressant imipramine is dissolved in physiological saline (three types of final concentrations 4, 8, and 16 mg/kg are prepared). Thereafter, the resultant drug is administered into the abdominal cavity 30 minutes before the second forced swimming test starts (a drug having each concentration is administered to each group as a positive control). In the negative control group, instead of the above-described OCT3 inhibitor, only a physiological buffer solution is continuously injected into the third cerebral ventricle in an administration method and an experimental schedule similar to those in the OCT3 inhibitor-administrated group to perform the forced swimming test.

In the above-described forced swimming test, a result similar to the result in the prior literature (Kitaichi. et al., Neurosci Lett. 2005 Jul. 1-8; 382 (1-2): 195-200) is estimated. That is, symptoms suggesting depression are caused in the negative control, and an immobility state is exhibited in most time of the 300 seconds of the swimming (an average value of the immobility time is about 200 seconds). It is expected that this immobility state is significantly reduced in the mice into which the OCT3 inhibitor in a sufficient amount with respect to the IC50 concentration has been continuously injected (0.25 µl/hr) (an average value of the immobility time is about 70 seconds). When a low dose of the antidepressant imipramine (4 mg/kg) or a low dose of the OCT3 inhibitor is administered alone (0.25 µl/hr), it is predicted that there is no difference in the immobility time in the forced swimming test from the negative control (an average value of the immobility time is about 200 seconds in both cases). However, when both are used together, it can be expected that the immobility state is significantly reduced with respect to the negative control (an average value of the immobility time is about 100 seconds). If the above-described results are obtained, the antidepressant effect of the OCT3 inhibitor is confirmed, and the combined effect thereof with imipramine can be also confirmed.

Example 4

Confirmation of Change in Spontaneous Movement Activity Before and after Administrating OCT3 Inhibitor In order to eliminate a possibility that "by administrating the OCT3 inhibitor, the spontaneous movement activity is enhanced, and the apparent immobility behavior is suppressed (there is no antidepressant effect)", the spontaneous movement activity before and after administrating the OCT3 inhibitor is measured in a similar manner to the prior literature (Kitaichi. et al., Neurosci Lett. 2005 Jul. 1-8; 382 (1-2): 195-200).

In an experiment, ddY male mice are used. The mice which have been bred for three days or more after the purchase are divided into two groups. The OCT3 inhibitor is continuously injected into the third cerebral ventricle in one of the groups with an osmotic pump based on the previous report (J. Chem. Neuroanat. 2000 20: 375-87). In the other group, a sham operation is performed, and a physiological buffer solution is injected into the third cerebral ventricle instead of the OCT3 inhibitor as a negative control. The mice one week after the injection are placed in a plastic cage (30 cm×35 cm×17 cm), and spontaneous momentum is measured before and after intravenous administration of a stimulant methamphetamine (1 mg/kg). The spontaneous momentum is automatically counted with an infrared sensor (Melquest Ltd., SCANET SV-10) mounted on the wall.

From 120 minutes before the administration of the stimulant methamphetamine until just before the administration, the spontaneous momentum in the negative control group and the spontaneous momentum in the OCT3 inhibitor-administrated group are measured. From just after the administration of methamphetamine until 180 minutes after the administration, stimulant-induced spontaneous momentum is measured in each group. After the measurement, a significant difference test is performed for the count number of the spontaneous momentum in each group using a Scheffe method. It is determined whether the spontaneous momentum changes statistically significantly (p-value is less than 0.05).

In the above-described spontaneous movement activity test, a result similar to the result in the prior literature (Kitaichi. et al., Neurosci Lett. 2005 Jul. 1-8; 382 (1-2): 195-200) is estimated. That is, before the administration of the stimulant methamphetamine, the count number of the spontaneous movement is almost the same between the negative control group and the OCT3 inhibitor-administrated group. After the administration of the stimulant methamphetamine, it is predicted that the count number in the OCT3 inhibitor-not administrated group is almost twice that in the negative control group and that the count number in the OCT3 inhibitor-administrated group is almost 5 times that in the negative control group. By performing the significant difference test for the count number, it can be expected that the following can be confirmed. That is, before the administration of the stimulant methamphetamine, there is no significant difference between the negative control group and the OCT3 inhibitor-administrated group, and the spontaneous momentum does not change by the administration of the OCT3 inhibitor. After the administration of the stimulant methamphetamine, it is expected that the spontaneous movement is statistically significantly enhanced more than before the administration. Therefore, it can be expected that confirmation that this test system functions effectively can be made. If the above results are obtained, it can be confirmed that the OCT3 inhibitor has no spontaneous movement activity. The reduced immobility time confirmed by the forced swimming test becomes a base for indicating the antidepressant effect.

INDUSTRIAL APPLICABILITY

The present invention can be utilized in a pharmaceutical industry.

The invention claimed is:
1. A method for the inhibition of an organic cation transporter 3 (OCT3) comprising administrating an OCT3 inhibitor represented by the following formula (I), a pharmaceutically acceptable salt thereof, or a pharmaceutically acceptable solvate thereof, as an active component, to a subject in order to inhibit the OCT3,

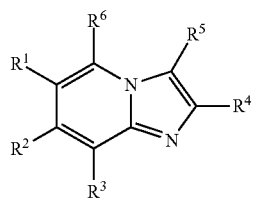

in formula (I)
$R^1$, $R^2$, $R^3$, $R^5$ and $R^6$ can be the same or different, and each represent a hydrogen atom or a methyl group, $R^4$ represents a group represented by formula (II),

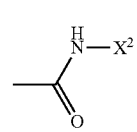

in formula (II),
$X^2$ represents any of the groups represented by the following formulae (1-1) to (1-26), wherein the most left carbon atom in the following formulae (1-1) to (1-26) represents a carbon atom which attaches to N in formula (II),

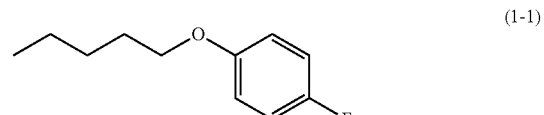

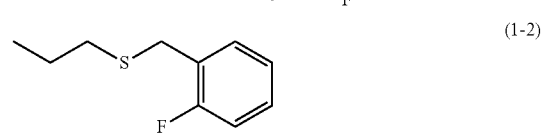

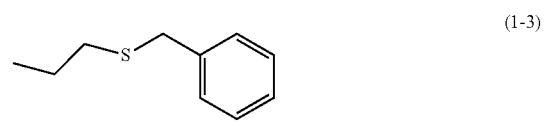

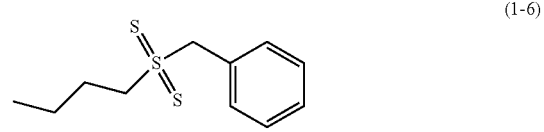

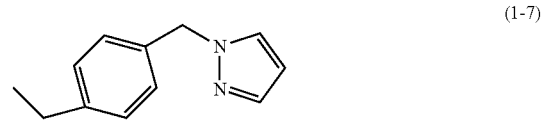

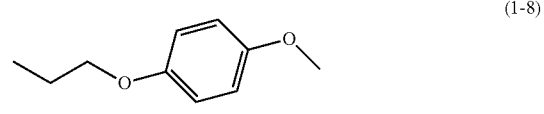

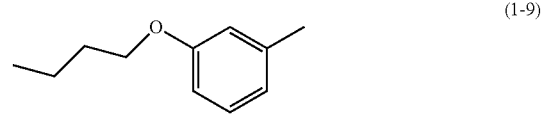

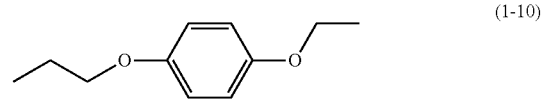

(1-11) 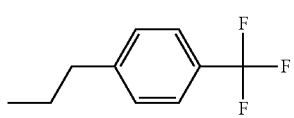

(1-12) 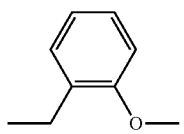

(1-13) 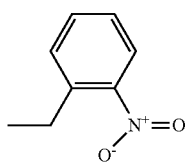

(1-14) 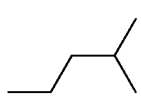

(1-15) 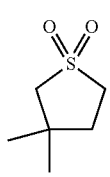

(1-16) 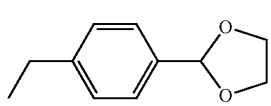

(1-17) 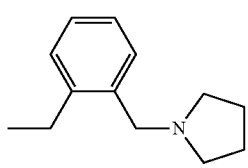

(1-18) 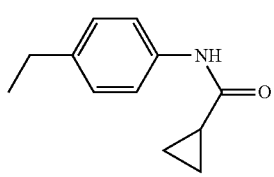

(1-19) 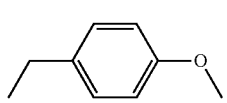

(1-20) 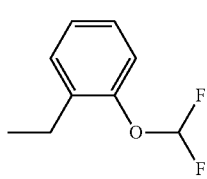

(1-21) 

(1-22) 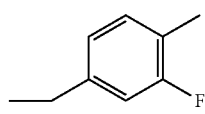

(1-23) 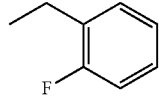

(1-24) 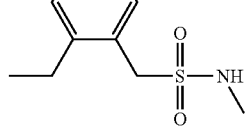

(1-25) 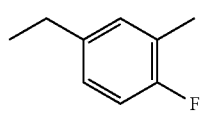

(1-26) 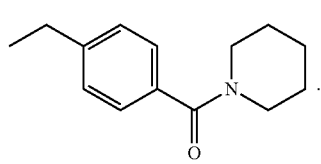

2. A method for the inhibition of an organic cation transporter 3 (OCT3) comprising administrating an OCT3 inhibitor represented by the following formula (I), a pharmaceutically acceptable salt thereof, or a pharmaceutically acceptable solvate thereof, as an active component, to a subject in order to inhibit the OCT3,

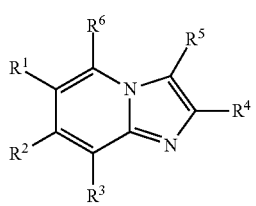

(I)

in formula (I)
$R^1$, $R^2$, $R^3$, $R^5$ and $R^6$ can be the same or different, and each represent a hydrogen atom or a methyl group,
$R^4$ represents following formula (2-1)' or (2-2)'

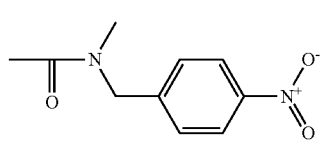

(2-1)'

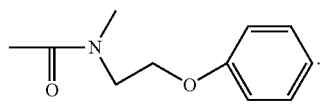

(2-2)'

3. The method according to claim 1, wherein the subject suffers from depression and the OCT3 inhibitor is administered by the subject to treat the depression.

4. The method according to claim 2, wherein the subject suffers from depression and the OCT3 inhibitor is administered by the subject to treat the depression.

* * * * *